United States Patent [19]

McIntyre

[11] 4,379,967

[45] Apr. 12, 1983

[54] FIBER OPTIC MATRIX CODING METHOD AND APPARATUS FOR RADIATION IMAGE AMPLIFIER

[76] Inventor: John A. McIntyre, 2316 Bristol St., Bryan, Tex. 77801

[21] Appl. No.: 180,331

[22] Filed: Aug. 22, 1980

[51] Int. Cl.³ .............................................. G02B 5/14
[52] U.S. Cl. .................................... 250/227; 250/368
[58] Field of Search ............ 250/213 R, 213 VT, 227, 250/368, 367, 369; 350/96.15, 96.16, 96.24, 96.25, 96.27

[56] References Cited

U.S. PATENT DOCUMENTS

| | | | |
|---|---|---|---|
| 3,652,855 | 3/1972 | McIntyre et al. | 250/227 |
| 3,758,780 | 9/1973 | Lee | 250/221 |
| 3,777,161 | 12/1973 | Lee | 250/361 |
| 3,996,455 | 12/1976 | Schaefer et al. | 250/227 |

OTHER PUBLICATIONS

Multi-Strip Scintillation Counter by Lee, Allred and Clark Nuclear Instruments and Methods, vol. 119 (1974) pp. 29-33.

*Primary Examiner*—David C. Nelms
*Attorney, Agent, or Firm*—Vinson & Elkins

[57] ABSTRACT

An improved fiber optic matrix coding method and apparatus for a radiation image amplifier is disclosed. The improved method and apparatus permits the determination of the location of detected incident radiation to within an area approximately equal to the cross-sectional area of one of the optical fibers in the coding matrix, thereby providing a four-fold reduction in the number of optical fibers currently required to obtain a radiation image of comparable resolution. The improved method and apparatus also yields a four-fold improvement in the resolution of the timing pulse, thereby permitting the achievement of correspondingly higher rates for processing radiation image data.

47 Claims, 20 Drawing Figures

FIBER OPTIC MATRIX CODING METHOD AND APPARATUS FOR RADIATION IMAGE AMPLIFIER

BACKGROUND OF THE INVENTION

The present invention relates to the field of electronic image display and more particularly to an improvement in the optical fiber coding method and apparatus of a radiation image amplifier.

Radiation image amplifiers are designed to detect patterns of radiation of relatively weak intensity, code the image of the pattern in the form of electrical signals, amplify such signals and present an enlarged and intensified visual display of the original radiation pattern. Such radiation image amplifiers locate the incident radiation by stopping the radiation in a scintillator. The light emitted at the location of the radiation stopped in the scintillator is transferred via an optical fiber array to photosensitive amplifiers such as photomultiplier tubes for conversion into electrical signals. The resulting electrical signals are further amplified to obtain the desired visual display. Such a radiation image amplifier has been described in U.S. Pat. No. 3,652,855 which issed Mar. 28, 1972 to McIntyre and Saylor and which is incorporated herein by reference for all purposes.

The image transmission section of a radiation image amplifier typically comprises an array of optical fibers optically coupled at one end to a scintillator and optically coupled at the other end to a bank of photomultiplier tubes. The fibers transmit light from the scintillator to the photomultipliers. The number of photomultipliers required to locate a particular scintillation can be minimized by utilizing an optical fiber coding method for matrixing the fibers with different photomultipliers.

The proper matrixing is accomplished by positioning the fibers with their input ends arranged in a matrix with one or more fibers covering each unit area of the field of the image to be detected. Each of the individual fibers in a given unit area is connected to a different photomultiplier tube, but fibers from different areas are connected to the same photomultiplier tubes in different combinations. With a matrix coding method, a large number of scintillation locations can be determined from a small number of photomultipliers. Such a matrix coding method has been described in U.S. Pat. No. 3,652,855.

Because many individual optical fibers must be used to make up a matrix and because the fibers are relatively expensive to install, it is desirable to minimize the number of fibers necessary to provide a radiation image. Since the level of image resolution is proportional to the number of fibers in the matrix, a reduction in the number of fibers used naturally impairs the resolution attainable. The existing problem is to attain an increased level of image resolution in a radiation image amplifier without a corresponding increase in the number of optical fibers in the fiber matrix. Stated alternatively, the problem is to reduce the number of optical fibers in the fiber matrix of a radiation image amplifier without a corresponding decrease in the image resolution attainable by said amplifier.

Radiation image amplifiers may be used as detectors in numerous applications. In particular, radiation image amplifiers have been used as real time detectors of gamma ray radiation for the stereoscopic viewing of annihilation radiation sources as described in U.S. Pat. No. 4,135,089 which issued Jan. 16, 1979 to McIntyre.

In such an application, the timing signal that is produced by the radiation image amplifier to indicate when each gamma ray is detected is used to determine the correlations between points associated with pairs of gamma rays. The rate at which such information may be processed is limited by the time resolution of the radiation image amplifier. Specifically, the more rapidly the radiation image amplifier can detect incident radiation the more effectively can accidental coincidence pulses be rejected.

Since the photomultipliers of a radiation image amplifier must obtain at least one photoelectron from a scintillation in order to detect a gamma ray, the time that is required to obtain that photoelectron is inversely proportional to the amount of light incident on the photomultipliers.

The existing problem is to reduce the time required by a radiation image amplifier to detect incident radiation and thereby increase the time resolution attainable by said amplifier in order to permit increased rates for processing radiation image data.

SUMMARY OF THE INVENTION

An object of the invention is to provide an improved matrix coding method and improved matrix coding apparatus for attaining increased levels of image resolution and time resolution in a radiation image amplifier.

Another object of the invention is to provide an improved matrix coding method and improved matrix coding apparatus for locating the position of a scintillation with an accuracy of one fiber diameter. As will be more fully discussed below, since the matrix coding method disclosed in U.S. Pat. No. 3,652,855 is capable of locating the position of a scintillation only with an accuracy of two fiber diameters, the present invention provides a four-fold reduction in the number of optical fibers required to produce an image without decreasing the level of image resolution.

Another object of the invention is to provide an improved matrix coding method and improved matrix coding apparatus for detecting and measuring a large optical signal arising from the scintillation caused by detected incident radiation. The detection of said signal permits a four-fold increase in the rate for processing radiation image data.

These and other features of advantage of this invention will be apparent from the drawings, the detailed description, and the appended claims.

DETAILED DESCRIPTION OF THE PREFERRED EMBODIMENTS

The coding method and apparatus of the present invention can be used with any scintillator device to determine the location at which energy is deposited in the scintillator by electromagnetic radiation or by energetic particles such as electrons, protons, mesons, etc. The term "radiation" as used herein will be understood to refer to particles as well as to electromagnetic energy.

Figure 1:
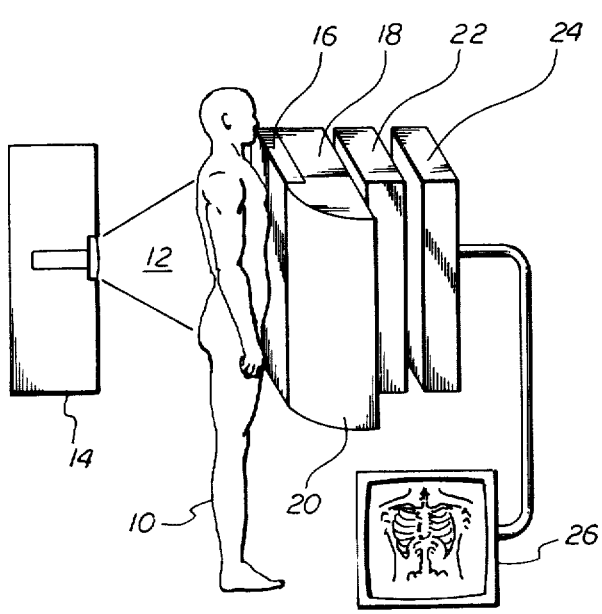
FIG. 1 is a diagrammatic view of a radiation image amplifier system being used in conjunction with a diagnostic gamma ray apparatus.

A particular preferred embodiment of the coding method and apparatus will be described in connection with a diagnostic gamma ray device in which a radiation image amplifier provides a simultaneous, detailed oscilloscope display of the gamma ray pattern. FIG. 1 depicts the exposure of a patient 10 to gamma ray radiation 12 from gamma ray source 14 such as radioactive Cobalt 60. The gamma rays are variously absorbed and deflected in reacting with the irradiated patient 10. The gamma rays which penetrate the body of the patient 10 form a particular radiation pattern which carries information concerning the internal structure of the patient's body. These information carrying gamma rays are intercepted by a scintillator 16 placed adjacent to the patient on the side of the patient opposite from that receiving the radiation 12. The face of the scintillator 16 has an area of sufficient extension to intercept the gamma rays of interest.

In the preferred embodiment of the invention, scintillator 16 converts the intercepted gamma rays into light signals which are detected and transmitted by a fiber optics array 18 and by a light pipe array 20. The fiber optics array 18 comprises a close-packed bundle of optical fibers with the input ends of the fibers placed adjacent to the face of the scintillator 16 that is furthest from the radiation source 14. The light pipe array 20 comprises a number of solid pieces of transparent material with the input ends of the pieces placed adjacent to an edge of the scintillator 16. The other ends of the optical fibers and light pipes terminate in photosensitive photomultiplier tubes located in the photomultiplier bank 22. The photomulitplier tubes detect and amplify the weak light signals to provide an electrical signal of sufficient strength to serve as input to the electronic logic circuitry 24.

The electronic logic circuitry 24 of the preferred embodiment of the invention provides electronic signals for deflecting the electron beam of the cathode ray tube of the display oscilloscope 26. For each gamma ray detected by the scintillator 16, the electron beam of the oscilloscope 26 is deflected to (x, y) coordinates that are proportional to the (x, y) coordinates of the gamma ray in the scintillator 16. The pattern of dots on the face of the cathode ray tube of the display oscilloscope 26 represents the locations of the gamma rays striking the scintillator 16. In this manner, a visual display is obtained that reflects the intensity of gamma ray radiation transmitted through the body of the patient 10.

CODING METHOD

Figure 2:
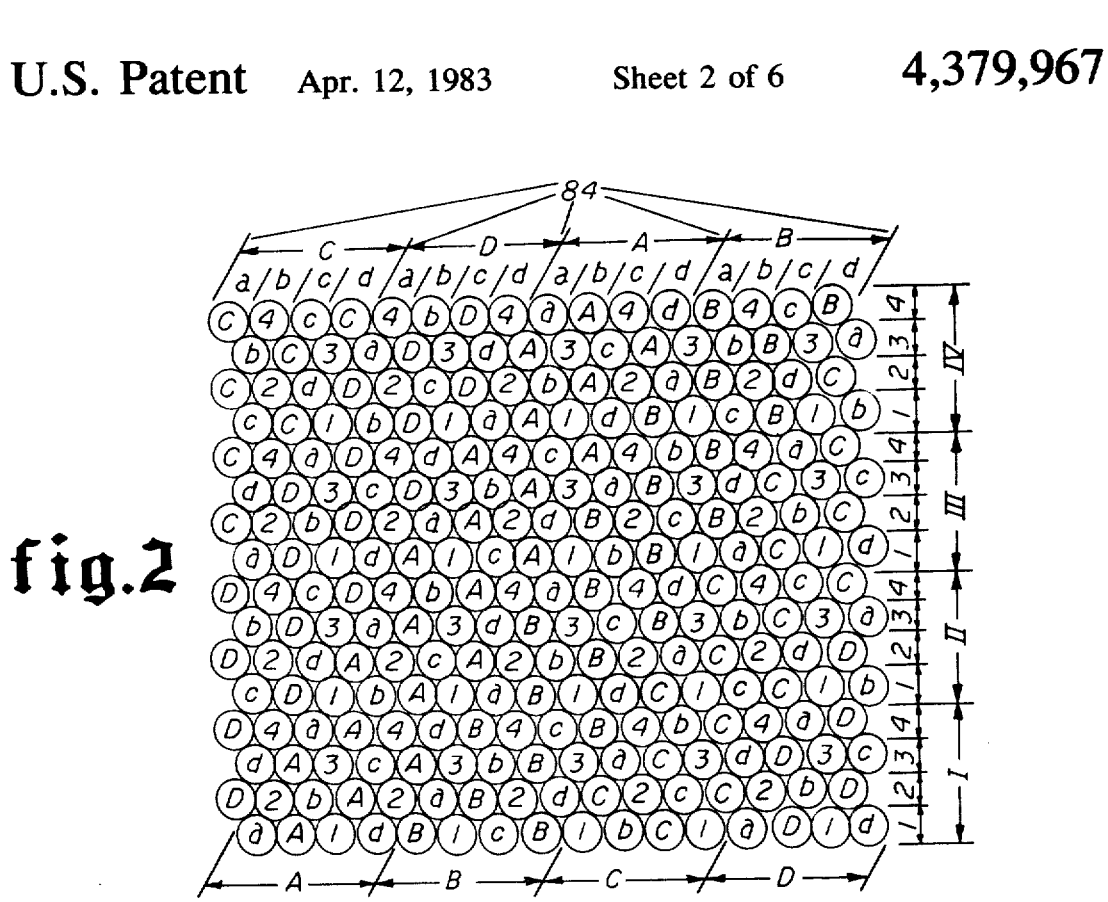
FIG. 2 is a diagrammatic representation of the ends of the close packed optical fibers composing the fiber optics array and a representation of the fiber matrix coordinate system used to determine scintillation locations.

The coding method of the preferred embodiment of the invention utilizes the matrix of optical fibers depicted in FIG. 2. Each numbered or lettered circle represents the end of an optical fiber 28 at the face of the scintillator 16. The number or letter in each circle denotes the photomultiplier to which the other end of the fiber is connected.

Inspection of the numbering system shows that each horizontal row has been assigned an Arabic number; that each group of four horizontal rows (a horizontal section) has been assigned a Roman numeral; that each column directed upward and approximately 30° to the right of the vertical has been assigned a small letter; and that each group of four columns (a vertical section) in this direction has been assigned a capital letter. The numbers for these assignments are indicated to the right of the fiber matrix and the letters for these assignments are indicated above and below the fiber matrix shown in FIG. 2. A combination of one small letter and one capital letter is sufficient to uniquely determine a column location. For example, the combination bA identifies the tenth column from the left at the top of FIG. 2. Such a combination of letters will be called the "address" of the column.

For any location in the fiber matrix, a circle of light with a diameter slightly greater than that of one fiber will cast light upon fiber ends having one number, one small letter, and one large letter. Furthermore, the center of each fiber end upon which light is cast lies within, at most, a fiber diameter of the center of the circle of light, i.e., within a fiber diameter of the location of the scintillation being detected. Thus, the fiber matrix "addresses" the scintillation location within the accuracy of the size of the elements in the matrix (one fiber diameter).

The significance of the improvement over the method described in U.S. Pat. No. 3,652,855 may be appreciated by considering a comparative example. In a typical 25 centimeter by 25 centimeter array of fibers in which each fiber has a fiber diameter of 1.00 millimeter, there are 250×250=62,500 fibers. Since the length of each fiber is about one meter, the total fiber length of the array is 62.5 kilometers (39 miles). With the present invention, fibers of 1.00 millimeter diameter can be used to obtain 1.00 milllimeter accuracy in locating the scintillation because the matrix coding method of the present invention is accurate to one fiber diameter. With the method used in U.S. Pat. No. 3,652,855, the accuracy is two fiber diameters. Thus, with that method, 0.50 millimeter diameter fibers would be required to obtain 1.00 millimeter accuracy. Since four times as many 0.50 millimeter fibers are required to cover the same area as 1.00 millimeter fibers, the length of fiber required would be increased from 39 miles to 155 miles, an increase of 116 miles.

Utilization of the fiber optic matrix coding method of the present invention reduces the number of photomultipliers required to locate the scintillation. Minimization of the number of photomultipliers is desirable since photomultipliers are much more expensive than the fibers.

In FIG. 2, the location of the fiber column nearest the scintillation is determined by 8 photomultipliers (a, b, c, d, A, B, C, D) even though there are 16 fiber columns to be addressed. In general, if there are m photomultipliers for the small letters (a, b, c, etc.) and M photomultipliers for the large letters (A, B, C, etc.), then m times M columns can be located (addressed) by the photomultipliers. In algebraic terms, if Pc is the number of photomultipliers addressing columns and C is the total number of columns, $$Pc = m + M \quad C = m + M \tag{1}$$

Thus, for $m=4$ and $M=4$ as shown in FIG. 2, $Pc = 4 + 4 = 8$ and $C = 4 \times 4 = 16$ as stated above. The advantages of the method become more apparent for larger arrays. Thus, if $m=40$, and $M=30$, $Pc = 40 + 30 = 70$ while $C = 40 \times 30 = 1200$, i.e., 70 photomultipliers can be used to determine 1200 column locations.

While there are two sets of lettered fibers to locate the columns in FIG. 2, there is only one set of numbered fibers with which to locate the rows. As explained below, a second set of numbers may be obtained by extracting the scintillation light from one edge (or perhaps two opposite edges) of the scintillator. In FIG. 2, the scintillator is divided into four horizontal sections numbered I, II, III and IV. Means for optically isolating the sections of the scintillator are provided so that the light from a single scintillation will be confined to a single horizontal section. In the preferred embodiment of the invention, four light transmitting pipes 30 (e.g., polished lucite pieces) are placed at the ends of these sections to transmit the light to photomultipliers labelled I, II, III and IV. In this manner, two sets of photomultipliers (1, 2, 3, 4 and I, II, III, IV) are used to address the 16 fiber rows in the array. As with the columns, if n is the number of photomultipliers with Arabic numbers and N is the number of photomultipliers with Roman numerals, then Pr, the number of photomultipliers for addressing the fiber rows, and R, the number of fiber rows, can be expressed as $$Pr = n + N \quad R = n \times N \tag{2}$$

Thus, if $n=50$ and $N=20$, $Pr = 50 + 20 = 70$, while $R = 50 \times 20 = 1000$, i.e., 70 photomultipliers can be used to determine 1000 row locations.

Locating (addressing) both the row and the column for a scintillation determines the location of the scintillation. If P is the total number of photomultipliers required and L is the total number of scintillation locations that can be determined (addressed), then, $$P = Pc + Pr \quad L = C \times R$$

or, $$P = m + M + n + N \quad L = m \times M \times n \times M \tag{3}$$

The reduction in P with respect to L is now particularly striking. If there are, for example, 1200 columns ($m=40$, $M=30$) and 1000 rows ($n=50$, $N=20$), then $P = 40 + 30 + 50 + 20 = 140$, while $L = 40 \times 30 \times 50 \times 20 = 1,200,000$. Thus, only 140 photomultipliers are required to address 1,200,000 scintillation locations. (Since it can be shown that the minimum number of photomultipliers is required when $m = M = n = N$, the above example is used to show only that m, M, n, and N can all be different if desired.)

SCINTILLATOR DESIGN

Figure 3:
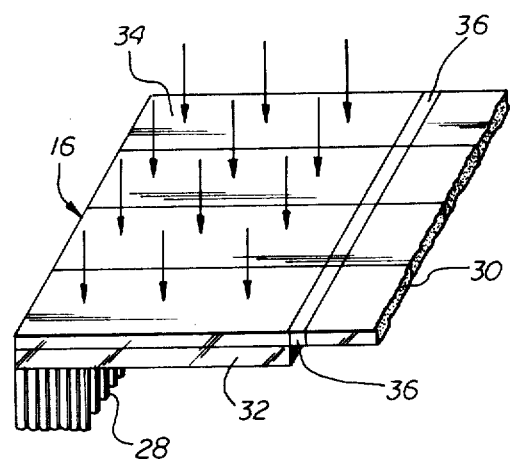
FIG. 3 is a diagrammatic representation of the scintillator screen showing how the optical fibers and the light pipes are optically coupled to the scintillator.

A drawing of the scintillator 16 is shown in FIG. 3. For efficiency in stopping gamma rays and for producing scintillations of short time duration, a thallium-activated sodium iodide crystal, NaI(Tl), is often selected as the scintillation material. A face window 32 of glass (or other suitable material) is optically coupled to the face of the scintillator 16 adjacent to the optical fibers 28 so that light can be transmitted to the ends of the optical fibers 28.

The scintillator 16 is divided into sections 34 such that each section 34 runs the length of the scintillator 16 in one direction. The scintillator sections 34 are divided by placing a very thin layer of aluminum foil between them or by leaving a very small air gap between the polished surfaces of the sections. An end window 36 of glass (or other suitable material) at one end of each section 34 transmits light from each section to a light pipe 30 of plastic (or other suitable material) which, in turn, transmits light to one of the photomultipliers. The face window 32 and the end window 36 are incorporated into a hermetically sealed enclosure which protects the hygroscopic NaI(T1) scintillator 16 from the atmosphere.

The edge of each scintillator section 34 opposite the end window 36 are polished and coated with reflecting material. Each of the mirror surfaces of the edges so treated serves to reflect light from the scintillations 38 back toward the end window 36. The face of each scintillator section 34 opposite to the face window 32 is also coated to provide a mirror surface which serves to reflect light from the scintillations 38 back toward the face window 32.

Figure 4:
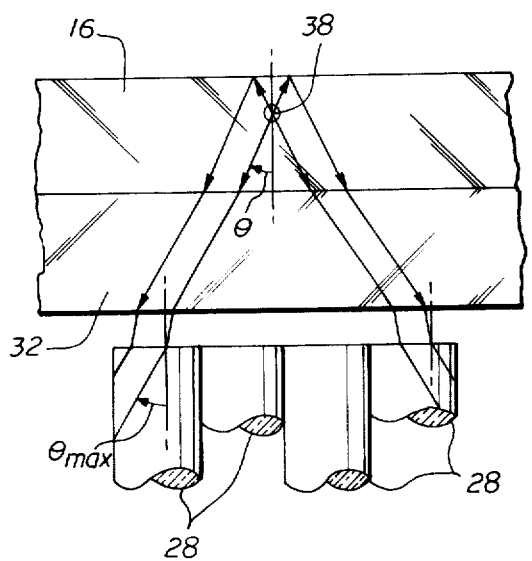
FIG. 4 illustrates the path of scintillation light from the scintillator to the optical fibers.

The paths of the light transmitted through the scintillator 16 and the face window 32 are shown in FIG. 4. Light is emitted from the scintillation 38 in all directions and at all angles of emission, but only those rays lying inside the cone of vertex angle $2\theta$ will be transmitted through the optical fibers 28. The largest emission angle $\theta$ for which light can be collected by a fiber 28 is determined by $\theta_{max}$, the maximum permissible angle in the fiber 28 for light transmission. ($\theta_{max}$ is measured from the normal to the fiber end face). If $n_f$ is the index of refraction of the material of the fiber 28 while $n_s$ is the index of refraction of the material of the scintillator 16, then Snell's Law gives the relation:

$$n_s \times \sin\theta = n_f \times \sin\theta_{max} \quad (4)$$

Since $n_s$, $n_f$ and $\theta_{max}$ are known, the emission angle $\theta$ can be calculated from Equation 4. As an example, for a NaI(Tl) scintillator, $n_s=1.77$, while for a standard plastic (Crofon) fiber, $n_f=1.49$ and $\theta_{max}=21°$. Then from Equation 4, $\theta=17.4°$ in the NaI(Tl) scintillator.

From the value of $\theta=17.4°$, one can determine the maximum fraction of the scintillation light that can be transmitted by the fibers 28. It may be shown by integration that the fraction of the scintillation light emitted into a cone with apex angle $2\theta$ is $(1-\cos\theta)/2$. For the value $\theta=17.4°$, the fraction expressed as a percentage of the total emitted scintillation light is 2.3%. One would expect to collect double this value, or 4.6% of the light, since the same amount of light is reflected from the face of the scintillator 16 opposite the face window 32.

The fraction of scintillation light collected must be spread over the surface area of the ends of three fibers in order to detect and record the location of a scintillation 38. Also, it has been empirically determined that there is an attenuation loss in the fibers such that only about one-third of the light entering the fibers is transmitted. Thus, each photomultiplier receives, finally, only $4.6\% \times \frac{1}{3} \times \frac{1}{3} = 0.5\%$ of the scintillation light.

Let T denote the time for the scintillator 16 to emit light after being excited by a gamma ray. Because the optical fibers 28 transmit such a small fraction of the scintillation light it is necessary to wait during the time interval T to collect as much light as possible. Otherwise, not even one electron will be produced at the photosensitive surface of the photomultiplier and there will be no output pulse. This interval of time required to detect each scintillation 38 is the factor which limits the rate at which gamma rays can be processed by the coding system. Thus, the low efficiency of the fiber in collecting light and the attenuation in the fiber during transmission of the light leads directly to a restriction in the rate for processing gamma rays.

Figure 5:
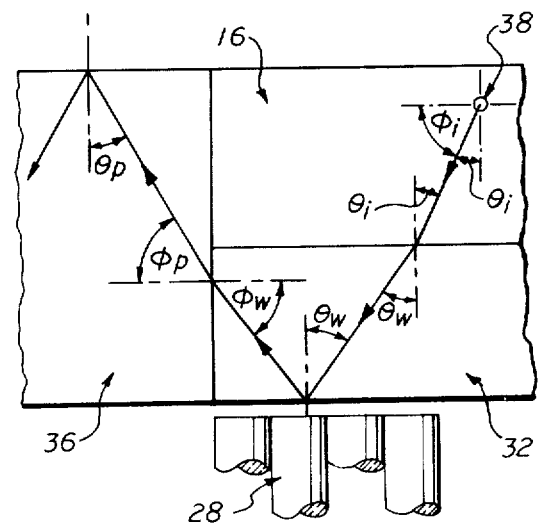
FIG. 5 illustrates one particular path of scintillation light from the scintillator to the end window.

This restriction on the processing rate can be reduced by a factor of 4 by collecting light from one edge of the scintillator 16 as well as through the fibers 28. As shown in FIG. 5, the amount of light collected at an edge will be restricted by the values of the angles $\theta_w$ and $\theta_p$, the minimum angles at which light will be internally reflected in the face window 32 and in the end window 36, respectively. (All the light rays from the scintillation 38 that strike the scintillator face opposite face window 32 are reflected by its mirror surface.)

The value for $\theta_i$ determined by $\theta_w$ is found by applying Snell's Law at the optical interfaces at the face window 32. To minimize $\theta_i$ (see below), a thin air gap (see FIG. 5) has been placed between the face window 32 and the optical fibers 28. (Because the light rays passing through the air gap that are accepted by the optical fibers 28 are nearly perpendicular to the surface of the face window 32, the air gap introduces only a 8% loss in light intensity for these rays.) Applying Snell's Law gives:

$$n_s \times \sin\theta_i = n_w \times \sin\theta_w = n_a \times \sin\theta_a \quad (5a)$$

where the subscript s refers to scintillator, the subscript w refers to window, and the subscript a refers to air.

For internal reflection at the air surface, $\theta_a=90°$. Since $n_a=1$, $$\sin\theta_i = 1/n_s \quad (6a)$$

The value of $\theta_i$ determined by $\theta_p$ in the end window can be calcuated in a similar manner. At the surface of the end window, Snell'Law gives (see FIG. 5)

$$n_p \times \sin\theta_p = n_a \times \sin\theta_a = 1$$

Thus, $$\sin\theta_p = 1/n_p \quad (5b)$$

At the interface between the end window and the face window, Snell's Law gives $$n_p \times \sin\phi_p = n_w \times \sin\phi_w \quad (5c)$$

Since the $\phi$'s and the $\theta$'s are complementary angles, $\sin\phi=\cos\theta$. Substituting these relations into Eq. 5c, we obtain $$n_p \times \cos\theta_p = n_w \times \cos\theta_w$$

$$n_p^2(1-\sin^2\theta_p) = n_w^2(1-\sin^2\theta_w) \quad (5d)$$

But $\sin\theta_p=1/n_p$ from Eq. 5b while $\sin\theta_w=(n_s/n_w)\sin\theta_i$. Substituting these relationships into Eq. 5d, we obtain $$n_p^2(1-1/n_p^2) = n_w^2(1-(n_s/n_w)^2\sin^2\theta_i)$$

$$n_p^2-1 = n_w^2 - n_s^2\sin^2\theta_i, \text{ and}$$

$$\sin^2\theta_i = (n_w^2-n_p^2+1)/n_s^2 \quad (6b)$$

It is instructive to note that Eq. 6a, which resulted from a single interface between the scintillator and the face window, is actually a special case of Eq. 6b. For, if we set $n_p=n_w$ in FIG. 5, then there is only one interface. Replacing $n_p$ by $n_w$ in Eq. 6b leads to $$\sin^2\theta_i = (n_p^2-n_p^2+1)/n_s^2$$

or, $\sin\theta_i=1/n_s$ as in Eq. 6a. Since $n_w$ and $n_p$ will ordinarily have the same value, we will use Eq. 6a to find $\theta_i$ for the light rays which enter the end window 36 from the face window 32 as in FIG. 5. Taking the value of $n_s=1.77$ (for NaI(Tl)), $\theta_i$ is calculated to be 34.4° and $\phi_i=55.6°$.

Equation 6b can also be used to find $\theta_i$ when the light ray enters the end window from the scintillator 16 rather than from the face window 32 as shown in FIG. 5. In this case $n_w=n_s$ (see FIG. 5) and Eq. 6b becomes $$\sin^2\theta_i = (n_s^2-n_p^2+1)/n_s^2 \quad (7)$$

We will, therefore, use Eq. 7 to find $\theta_i$ for the light rays which enter the end window 36 from the scintillator 16. Taking $n_s=1.77$ and $n_p=1.49$, we obtain, for this case, $\theta_i=51.4°$ and $\phi_i=38.6°$.

Now it can be shown that with the face window and scintillator thicknesses used (see below) that above half of the light rays enter the end window 36 from the face window 32 and about half from the scintillator 16. We thus take the average value for $\phi_i$ to be $(55.6°+38.6°)/2=47.1°$.

So far, the analysis for the acceptance angle has been for a vertical slice through FIG. 3. For a horizontal slice, the boundaries between the scintillator sections 34 are air. Thus, in terms of the previous analysis, all horizontal rays enter the end window directly from the scintillator at $\phi_i=38.6°$. Finally, the horizontal and vertical $\phi_i$ values are averaged to give $(38.6°+47.1°)/2=42.9°$.

One can now calculate the fraction of the scintillation light lying within the cone with apex angle $2\phi_i$. This is the fraction that will be transmitted through the end window. As noted before, if a mirror is used to reflect the light in the cone facing the opposite direction, the fraction of the light transmitted down the pipe from the two cones is $1-\cos\phi_i$. Substituting in the average value of 42.9° for $\phi_i$ as calculated above, we obtain $$\text{Fraction of Light} = 1-\cos\phi_i = 0.27. \tag{8}$$

One now assumes, as before, a factor of 3 attenuation in the transmission of the light to the photomultiplier by the end window 36 and the light pipe 30, and obtains a collection efficiency of 27%/3=9%. Since the fraction of light transmitted by each fiber 28 was shown to be 0.5%, the amount of light collected by a photomultiplier optically coupled to the end window 36 of the scintillator 16 is 9%/0.5%=18 times as great as that transmitted to a photomultiplier coupled to the end of a fiber 28. Photoelectrons will be produced at a rate 18 times greater than the rate for the photomultipliers connected to the fiber ends.

Now, the width of the logic pulses to be generated by the scintillation light depends on the time "jitter" in the light emission. For example, the electrical logic pulse is initiated when the electrical scintillation pulse rises above a certain electrical threshold. Because of the time "jitter" there is a range of times during which different scintillation pulses will cross the threshold. To obtain reliable coincidence detection, then, the logic pulse widths must be wider than the "jitter" time. Now, it is well known that the time "jitter" is proportional to the square-root of the number of photons of light collected. (Statistical effects usually depend on the square-root of random numbers.) Thus, the light gain of 18 calculated above leads to a reduction of a factor of the square-root of 18 or about 4 in the time "jitter". Hence, the width of the logic pulses can be reduced a factor of 4.

Since the information from the photomultipliers at the fiber ends must be used to obtain the location (address) of the scintillation 38, the time restriction of $\Delta T$ at the fiber photomultipliers will still limit the rate at which scintillator addresses can be generated. However, in many applications a large fraction of the scintillations detected need not be processed. For example, in a coincidence counting system with two detectors, the other detector may not have been activated during the interval of observation. The undesired scintillations can then be rejected at a rate limited only by the time "jitter" associated with the large amount of light collected at the end window.

The thickness of the face window 32 and the scintillator 16 is determined empirically. Referring to FIG. 4, one sees that face window 32 must be thick enough so that the cone of light from a scintillation 38 near the face window 32 will spread over an area large enough to cover a significant part of three fibers. Inspection of FIG. 2 shows that a cone diameter of one fiber will usually satisfy this condition. The apex angle of the cone of light, $2\theta$, is determined, as already seen, by the maximum acceptance angle of the fibers, thereby determining the face window thickness. On the other hand, the thickness of the scintillator 16 is limited by the requirement that the light reflected by the top face of the scintillator 16 not spread over too many fibers; otherwise, light will enter fibers several diameters away from the scintillation 38 and an erroneous location will be obtained for the scintillation 38. To satisfy this condition, the maximum cone diameter has been selected to be that of 3 fibers. Using the index of refraction of 1.77 for NaI(T1) and 1.50 for the glass window, these restrictions lead to a face window thickness of about 1.3 fiber diameters and a scintillator thickness of about 1.6 fiber diameters.

As already mentioned, the light from the scintillator 16 is collected by optical fibers 28. Plastic (lucite core) fibers are available from DuPont under the trade name Crofon with fiber diameters ranging from 0.010 inch to 0.065 inch. Glass fibers with smaller diameters may be obtained from American Optical, Corning Glass, and Bendix. Standard diameters are in the 0.002 inch range.

The light pipes 30 connecting the edge of the end window 36 and the scintillator 16 to the appropriate photomultipliers can be made of transparent plastic such as lucite. Light which escapes from the ends of the scintillator sections 34 through end window 36 and into the light pipes 30 will internally reflect from the polished walls of the plastic. Alternatively, the walls can be coated with a reflecting material to give a mirror surface toward the light; then $\theta_p$ will be 90° and $\theta_w$ will determine $\theta_i$ and $\phi_i$.

ELECTRONIC PROCESSING CIRCUITS

Figure 6:
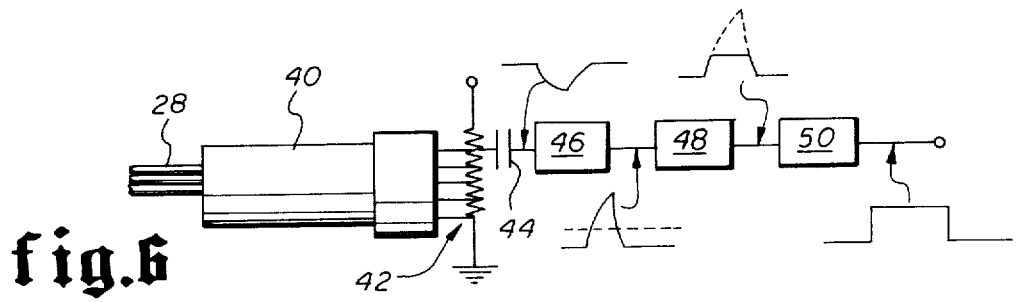
FIG. 6 is a diagrammatic representation of the electronic circuitry that detects scintillation light and then generates, amplifies and shapes a logic pulse to electronically represent the detected scintillation.

The optical fibers 28 and light pipes 30 transmit the light from the scintillator 16 to the photomultipliers 40 according to the coding system shown in FIG. 2. The fibers and light pipes terminate at photomultiplier photosurfaces as shown in FIG. 6. The photomultiplier 40 converts the light photons to electrons and multiplies the number of electrons by a large factor of the order of a million. Voltage for operating the photomultiplier 40 is taken from points along a voltage-divider network 42. The light flash from the scintillator 16 ultimately produces a voltage pulse at the output of the photomultiplier 40 which passes through a blocking capacitor 44 to an amplifier 46. The amplifier 46 increases the pulse magnitude sufficiently so that an adjustable discriminator level can be applied to reject pulses smaller than a selected size. A multivibrator 50 following the discriminator 48 is triggered by the pulses passing through the discriminator 48 and gives a standard logic pulse at the multi-vibrator output. The pulse shapes at the different stages of the discrimination process are shown in FIG. 6.

Figure 7:
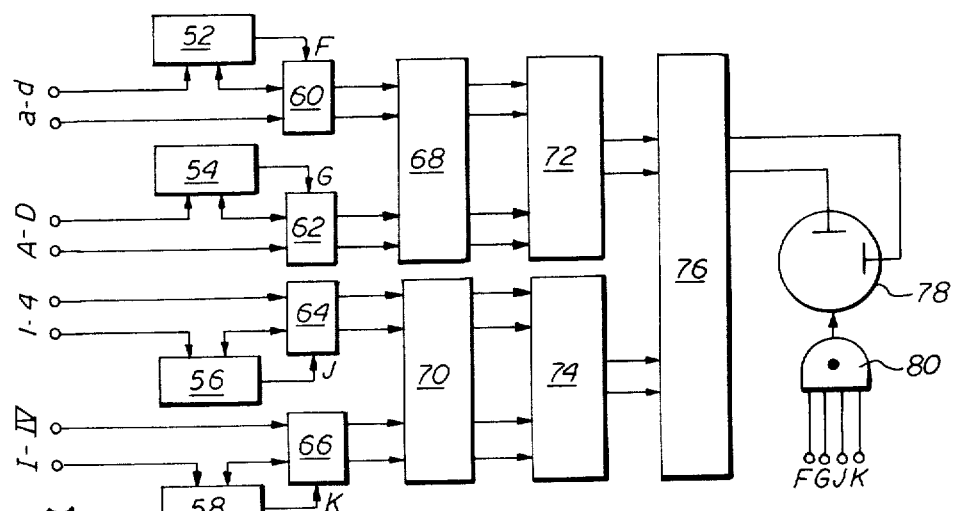
FIG. 7 is a block diagram representing the major elements in the electronic logic circuitry that processes the logic pulses that represent detected scintillations.

A block diagram of the electronic logic circuitry 24 is shown in FIG. 7. Lines from the photomultipliers 40 enter at the left. The lines proceed to SELECT circuits 52, 54, 56 and 58 and to GATES 60, 62, 64 and 66. Inspection of FIG. 2 shows that, for a circle of light with a diameter less than 3 fiber diameters, almost all of the light is collected by fibers that lie within one letter (or one number) of each other. The function of the SELECT circuits is to identify scintillation events for which one photomultiplier or two neighboring photomultipliers are activated. When such an event has been identified, pulses appear on lines F, G, J and K, and the GATES 60, 62, 64 and 66 are opened so that the pulses from the photomultipliers can be transmitted to the TRANSLATE stages 68 and 70.

These TRANSLATE stages resolve ambiguous addresses for the location of the scintillation caused by the acceptance of pulses from neighboring photomultipliers. For example, when pulses for two capital letters appear, two column sections are indicated (say, both A and B in FIG. 2). The location for the scintillation is known only to be in one of the two sections and a unique address cannot be determined. The TRANSLATE stages eliminate these ambiguities.

The pulses leaving these TRANSLATE stages in FIG. 7 are now on the proper lines for conversion to binary addresses in the BINARY CONVERSION processor 72 and 74. The outputs of these processors go to the DIGITAL-TO-ANALOG processor 76 which produces the x- and y-deflection signals for the cathode-ray tube (CRT) 78 of the display oscilloscope 26. The dot on the display screen of the oscilloscope 26 will be located at the position that corresponds to the location of the initial light flash in the scintillator 16. The electron gun of CRT 78 is activated only when the SELECT circuits 52-58 have determined that valid scintillation events have occurred. The gun is gated on, therefore, by output pulses from AND gate 80. AND gate 80 provides an output pulse only when all four SELECT circuits 52-58 provide output pulses at F, G, J and K.

A. SELECT Circuits

Figure 8:
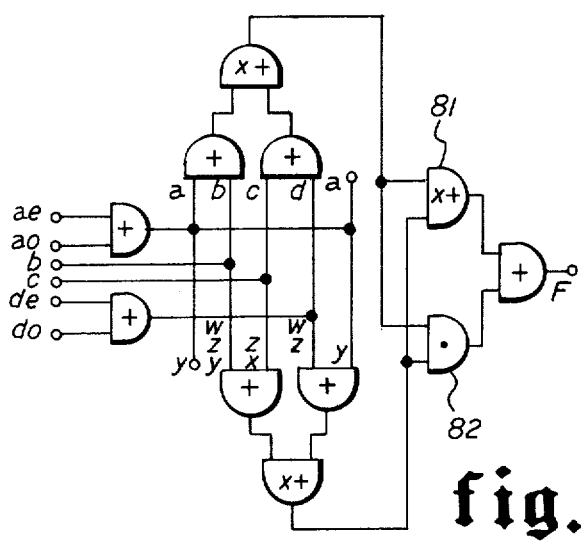
FIGS. 8 and 9 are logic diagrams illustrating the operation of the circuitry that selects single logic pulses and adjacent pairs of logic pulses.

The logic diagram for SELECT circuit 52 in FIG. 7 is shown in FIG. 8. The photomultiplier lines coming in at the left of FIG. 8 carry pulses originating from the column fibers a, b, c, and d, in FIG. 2. It will be noted that, instead of the four lines a, b, c, and d, there are six lines, ae, ao, b, c, de, and do. The extra "a" and "d" lines are used in the subsequent TRANSLATE section 68 (see FIG. 7). The designation ae is for the "a" fibers that lie in sections B and D (the even sections) and the designation ao is for fibers that lie in sections A and C (the odd sections). Similarly, there are two photomultipliers de and do for the "d" fibers.

The purpose of the circuit shown in FIG. 8 is to reject all combinations of pulses on the six lines except for single pulses or pairs of pulses on adjacent lines. The success of the circuit in accomplishing its purpose can be demonstrated with test pulses. First, consider a test pulse, x, on line c. It is seen that x is transmitted by all the OR and EXCLUSIVE OR (XOR) circuits except the last XOR circuit 81 and is transmitted to point F by the AND circuit 82. Second, consider a neighboring pair of pulses, y, on line ao and b. It is seen by tracing the y pulses through the circuit that the y pulses also produce a pulse at point F. However, in this case the AND circuit 82 does not transmit a pulse but the XOR circuit 81 does. Third, consider a group of these pulses, z, on lines b, c and de. It is seen that the XOR circuits prevent a pulse from reaching point F. Fourth, consider two non-adjacent pulses, w, on lines b and de. Again, the XOR circuits prevent a pulse from reaching point F. Thus, only single pulses such as x or a pair of adjacent pulses such as y will produce an output pulse at F. The pulse at F is used to open the normally closed GATE 60 in FIG. 7 so that the pulses can proceed to the TRANSLATE circuit 68.

The circuit in FIG. 8 is used for both SELECT 52 and SELECT 56 in FIG. 7. In order to accurately represent the SELECT 56 circuitry one need only re-label the circuit in FIG. 8 with the input line designations 1e, 1o, 2, 3, 4e and 4o. The extra "1" and "4" lines are used in the subsequent TRANSLATE section 70 (see FIG. 7). The designation 1e is for the "1" fibers that lie in sections II and IV (the even sections) and the designation 1o is for fibers that lie in sections I and III. (the odd sections). Similarly, there are two photomultipliers 4e and 4o for the "4" fibers. The output line of SELECT 56 is designated J (see FIG. 7) and it is used in a manner similar to F.

Figure 9:
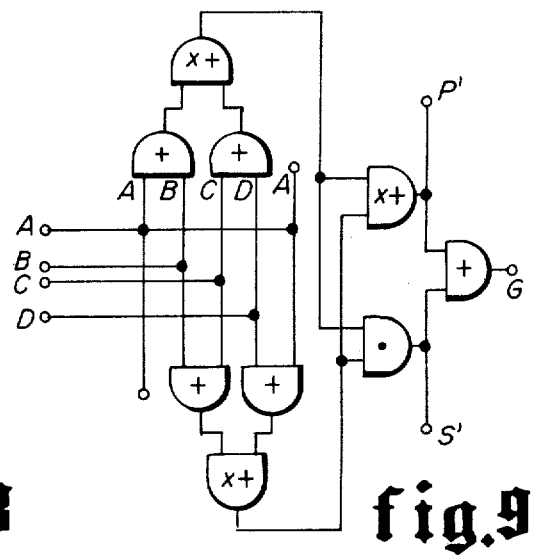

For SELECT 54 and SELECT 58 in FIG. 7, the circuit in FIG. 9 is used. In principle, this circuit is equivalent to that in FIG. 8. The only difference is that only 4 photomultipliers A, B, C and D are needed for the four column sections of SELECT 54. A pulse appears at point G in FIG. 9 if there is a pulse on one line or on two adjacent lines of SELECT 54.

Similarly, the circuit in FIG. 9 as used in SELECT 58 receives inputs from the photomultipliers I, II, III and IV connected to the four light pipes 30 receiving light originating in the respective horizonal sections 34 of the scintillator 16. A pulse appears at point K (see FIG. 7) if there is a pulse on one line or on two adjacent lines of SELECT 58.

B. GATE Circuits

Figure 10:
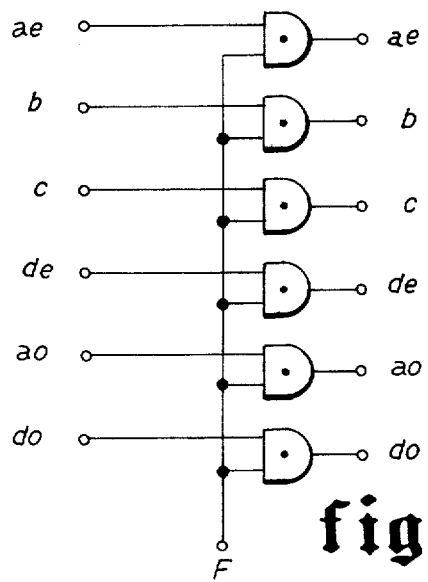
FIG. 10 is a logic diagram illustrating the operation of the gating circuitry.

The GATE circuits 60, 62, 64 and 66 are normally closed. They are opened by pulses on lines F, G, J and K respectively. A logic diagram of a GATE with 6 input lines (GATES 60 and 64) is shown in FIG. 10. GATES 62 and 66 are similar to GATES 60 and 64 except that GATES 62 and 66 each have 4 input lines.

The GATE circuit in FIG. 10 consists of an AND gate for each input line. One input line of each AND gate is connected to the gating line F. A pulse on line F allows each AND gate to give an output pulse if there is a pulse on the other input line of that AND gate.

C. TRANSLATE Circuits

The TRANSLATE circuit 68 solves the problem presented by the fact that scintillations occur near the seams 84 of the vertical sections of the fiber array 18. The term "seam" 84 refers to the boundary region between two adjacent sections of the fiber array 18 as shown in FIG. 2. In actuality, there is no physical separation between the sections of the fiber array 18. The sections are merely groups of four columns of fibers in the array symbolically designated in accordance with the coding method herein disclosed.

Scintillations occurring near these vertical seams 84 can easily produce false addresses. For example, a scintillation near the seam between A and B can provide light for fibers A, B, a and d. However, if only photomultipliers B and d convert the light to an electrical signal, the address provided will be Bd which is an address next to the seam between sections B and C rather than the correct address Ad or Ba next to the seam between sections A and B.

Because of such problems, the "a" and "d" fibers have each been divided into two groups, those fibers lying in odd sections (A and C) and those fibers lying in even sections (B and D). The odd lines are designated ao and do; the even lines are designated ae and de.

The first function of the TRANSLATE circuit 68 is to provide logic pulses which will indicate whether a single pulse or a pair of pulses have been produced by the fibers adjacent to the seams. All of the section fibers A, B, C, D lie near seams and the occurrence of single pulses and pairs of pulses among these fibers is determined by the SELECT circuit 54 shown in FIG. 9. Thus, if a single pulse has occurred a pulse will appear at point S' in FIG. 9 and if a pair of adjacent pulses has occurred a pulse will appear at point P'.

Figure 11:
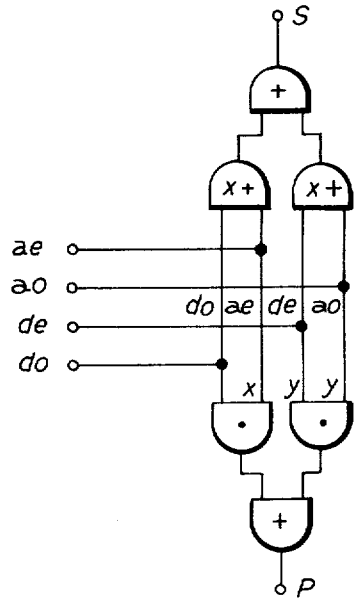
FIG. 11 is a logic diagram illustrating the operation of the circuitry that identifies logic pulses from scintillations occurring in the boundary region between two adjacent vertical sections of the fiber array.
Figure 13:
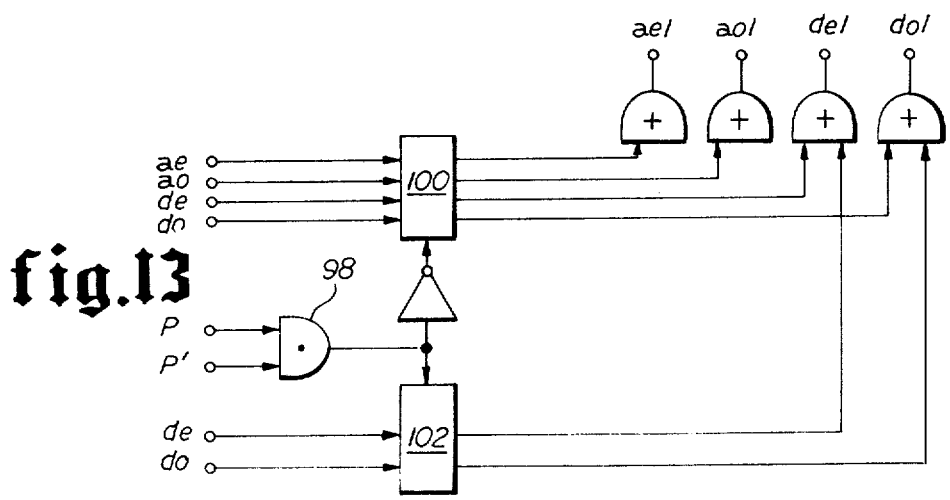
FIGS. 12, 13, 14, 15 and 16 are logic diagrams illustrating the operation of the circuitry that detects and corrects false scintillation addresses for scintillations occurring in the boundary region between two adjacent vertical sections of the fiber array.

The other fibers near seams 84 are the "a" and "d" fibers which have been designated ae, ao, de and do. If pairs of pulses occur between adjacent fibers, they can only occur between de and ao or between do and ae. The circuit shown in FIG. 11 identifies the single pulses and pairs of pulses among these a and d lines. For example, inspection of FIG. 11 reveals that a single test pulse, x, on line ae passes through the XOR and OR circuits to produce a pulse at point S, while the AND circuits prevent the pulse from reaching point P. Conversely, a pair of test pulses, y, on lines de and ao pass through the AND circuit to produce a pulse at point P, while the XOR circuit prevents the pulses from reaching point S. Since pulse pairs occur only for the combinations de-ao and do-ae, the circuitry will not be required to handle any other combinations of a and d pulses.

There are four possible combinations of single and paired pulses that must be considered:

(1) Pairs of pulses for the a and d lines and pairs of pulses for the A to D lines. (Pulse at P in FIG. 11 and pulse at P' in FIG. 9.)

(2) Single pulse for the a and d lines and pairs of pulses for the A to D lines. (Pulse at S in FIG. 11 and pulse at P' in FIG. 9.)

(3) Pairs of pulses for the a and d lines and a single pulse for the A to D lines. (Pulse at P in FIG. 11 and pulse at S' in FIG. 9.)

(4) Single pulse for the a and d lines and a single pulse for the A to D lines. (Pulse at S in FIG. 11 and pulse at S' in FIG. 9.)

The logic circuits for processing these combinations will now be described individually.

Figure 12:
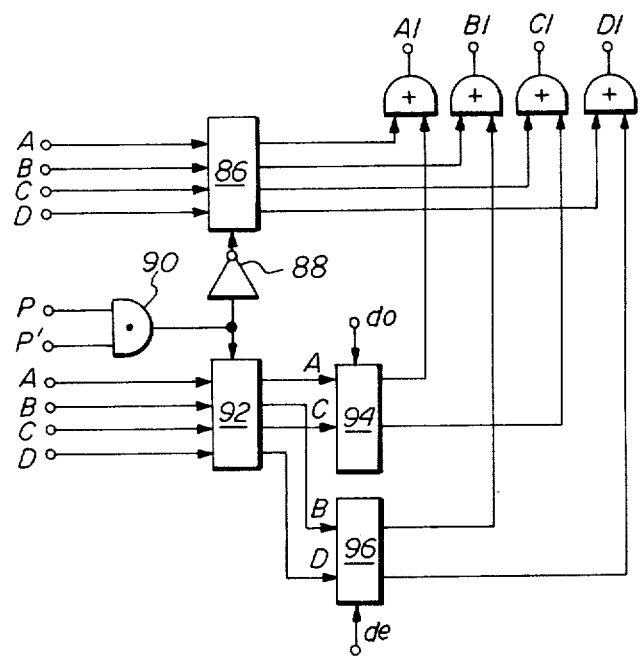

Combination (1): The logic circuit for combination (1) is shown in FIG. 12. Lines A to D enter GATE 86. GATE 86 and the other GATES in FIGS. 12–16 are AND type GATES similar to that shown in FIG. 10 with an AND gate for each input line. Since the gating pulse for GATE 86 enters through inverter 88, a zero voltage level at the input of inverter 88 will produce a positive level voltage at the gate input to GATE 86 and GATE 86 will be open so long as no pulse appears on the input line of inverter 88. However, for combination (1) above, pulses on lines P and P' open AND gate 90 in FIG. 12 and a positive pulse is applied to the input line of inverter 88. A zero voltage is applied, therefore, to the gating input of GATE 86 and GATE 86 is closed. At the same time, GATE 92 is opened and the pulses on lines A, B, C, D are transmitted through GATE 92. The result of having pulses satisfying combination (1) is to stop the A to D pulses that would be transmitted undisturbed through GATE 86 and route these pulses through GATE 92 to GATES 94 and 96.

The odd and even section lines (A, C and B, D respectively) are separated after GATE 92 so that the odd lines go to GATE 94 and the even lines to GATE 96. If the d-line carrying a pulse belongs to an odd section (A or C), then there is a pulse on line do and GATE 94 is opened while GATE 96 remains closed. A pulse on line A or C is thus transmitted to the output line A1 or C1. Similarly, if the d-line pulse belongs to an even section, the pulse on line de opens GATE 96 while GATE 94 remains closed. The pulse on the even section line, B or D, is then transmitted to the output B1 or D1.

To complete the pulse selection, one eliminates one of the lower case letter line pulses so that the final address will contain only one lower case letter and its associated capital letter. Since the capital letter chosen is associated with the d-line, one eliminates the a-line pulse utilizing the circuit shown in FIG. 13. As in FIG. 12, a P pulse coincident with a P' pulse in AND gate 98 closes the upper GATE 100 and opens the lower GATE 102. Only the two d-lines are passed through the lower GATE 102. Since the pair of pulses must lie on adjacent lines (see FIG. 8) only one d-line has a pulse; the other pulse must be on one of the a-lines which has been eliminated. Thus, the column lines ae1, ao1, de1, do1 have one pulse (on a d-line) as do the section lines A1, B1, C1, D1 (see FIG. 12). Furthermore, the pulse on the section lines is from the section containing the fiber feeding the d-line. Thus, the d-line pulse and the section line pulse give the correct column address for the scintillation to within one-half a fiber diameter (an error of one-half a diameter can occur because the a-line pulse has been dropped).

Figure 14:
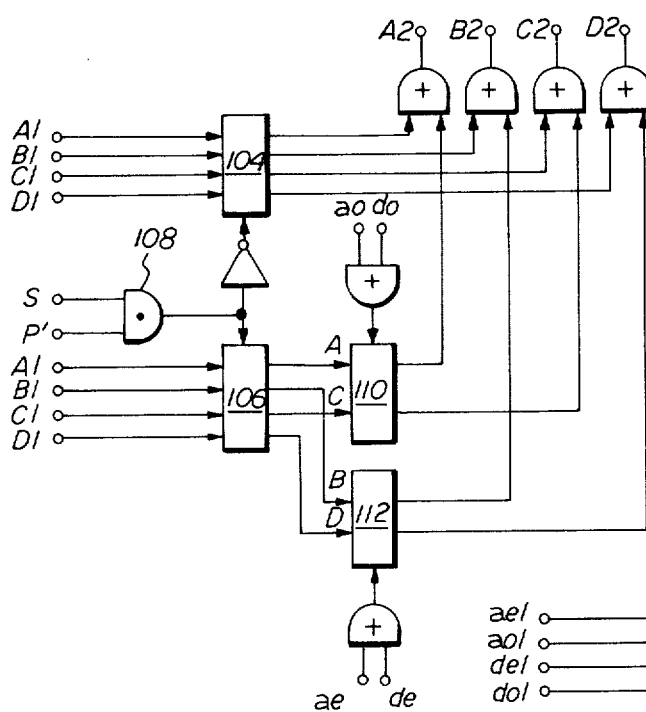

Combination (2): The logic circuit for translating the column address of combination (2) is shown in FIG. 14. The input lines to GATES 104 and 106 (see FIG. 14) are the output lines from FIG. 12. The gating pulses are obtained from the output of AND gate 108 which gives an output pulse when a pulse appears simultaneously on S (see FIG. 11) and on P' (see FIG. 9). As with combination (1), the output pulse from AND gate 108 closes GATE 104 which is normally open and opens GATE 106 which is normally closed. Thus, except for the situation where there are pulses at both S and P', the pulses at A1, B1, C1, D1 will be transmitted directly to the output lines A2, B2, C2, D2. When there are pulses at both S and P', the pulses will be routed through GATE 106.

The section lines leaving GATE 106 are separated into odd (A and C) and even (B and D) lines. These lines enter GATES 110 and 112 which are normally closed. GATE 110, the odd gate, is opened if a pulse appears on either of the odd column lines ao or do, while GATE 112 is opened if a pulse appears on either of the even column lines ae or de. Since only one of the column lines has a pulse, only one GATE (110 or 112) will be opened and the section line associated with the column line will be connected to the output lines A2, B2, C2, D2. Again, an address with one column letter and its associated section letter is obtained.

Figure 15:
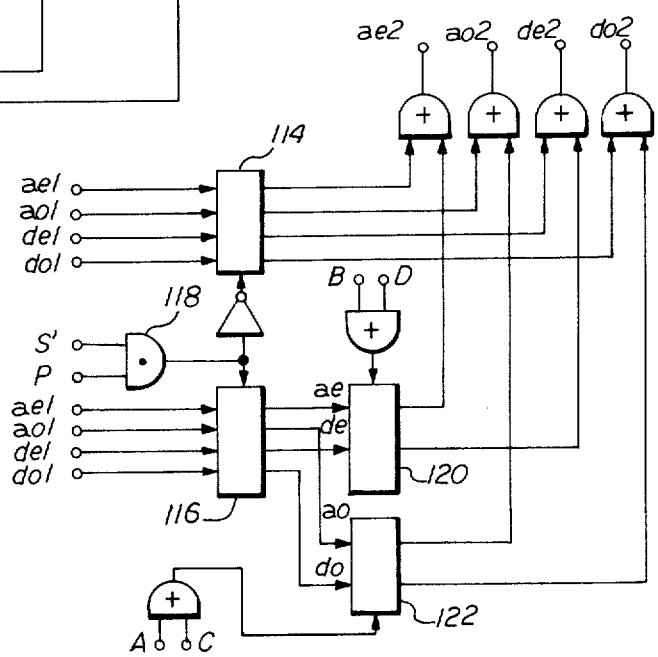

Combination (3): The logic circuit for translating the column address of combination (3) is shown in FIG. 15. The input lines to GATES 114 and 116 are the output lines from FIG. 13. The gating pulses are obtained from the output of AND gate 118 which gives an output pulse when a pulse appears simultaneously on P (see FIG. 11) and on S' (see FIG. 9). As with combinations (1) and (2), the output pulse from the AND gate closes one GATE (114) which is normally open and opens one GATE (116) which is normally closed. Thus, except for the situation where there are pulses at both P and S', the pulses on ae1, ao1, de1, do1 will be transmitted directly to the output lines ae2, ao2, de2, do2.

However, when pulses do appear simultaneously at P and S', the pulses on the input lines are transmitted through GATE 116. These lines are divided into two groups, those lines ae and de coming from even sections go to GATE 120, those lines ao and do coming from odd sections go to GATE 122. GATE 120 is opened by pulses coming from the even section lines (B or D), while GATE 122 is opened by pulses coming from the odd section lines (A or C). Since there is only one pulse on lines A, B, C, D, only one GATE (120 or 122) will open. Furthermore, the column pulses must be on adjacent lines (either de-ao or do-ae). Thus, only one column pulse will reach the output lines ae2, ao2, de2, do2. Again, a pair of pulses is selected which produce a correct column address (to within one-half a fiber diameter).

Figure 16:
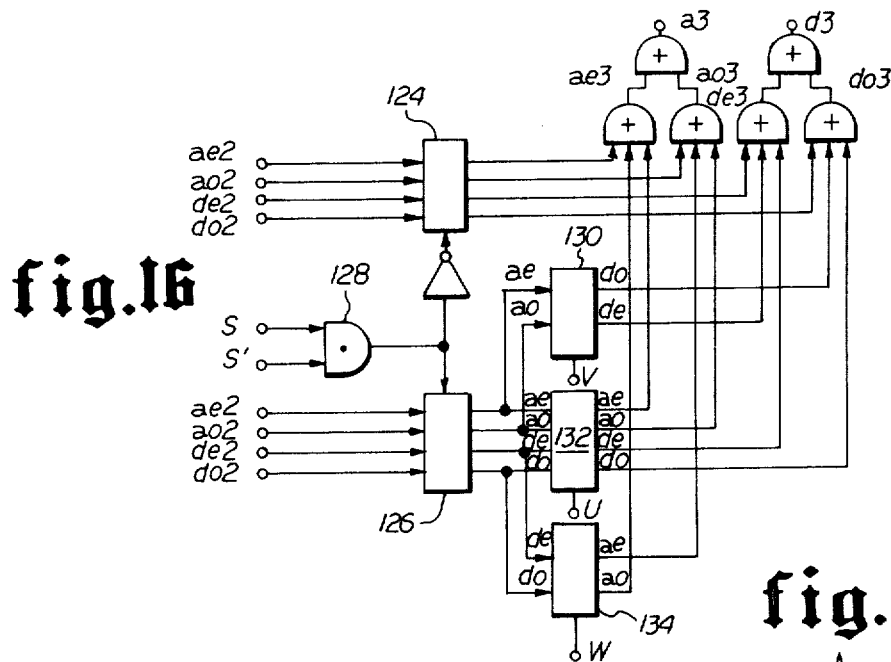

Combination (4): The logic circuit for translating the column address of combination (4) is shown in FIG. 16. The input lines to GATES 124 and 126 are the output lines from FIG. 15. The gating pulses are obtained from the output of AND gate 128 which gives an output pulse when a pulse appears simultaneously on S (see FIG. 11) and on S' (see FIG. 9). As with combinations (1), (2) and (3), the output pulse from the AND gate closes one GATE (124) which is normally open and opens one GATE (126) which is normally closed. Thus, except for the situation where there are pulses at both S and S', the pulses on ae2, ao2, de2, do2 will be transmitted to the output lines ae3, ao3, de3, do3, and finally combined into two lines a3 and d3. As explained below, lines a3 and d3 are later used to obtain a binary form of the column address of the scintillation.

The lines leaving GATE 126 are separated into three groups which enter GATES 130, 132 and 134. When opened by a pulse at U, GATE 132 transmits pulses on all four lines; when opened by a pulse at V, GATE 130 transmits only pulses on lines ae and ao; when opened by a pulse at W, GATE 134 transmits only pulses on lines de and do.

Figure 17:
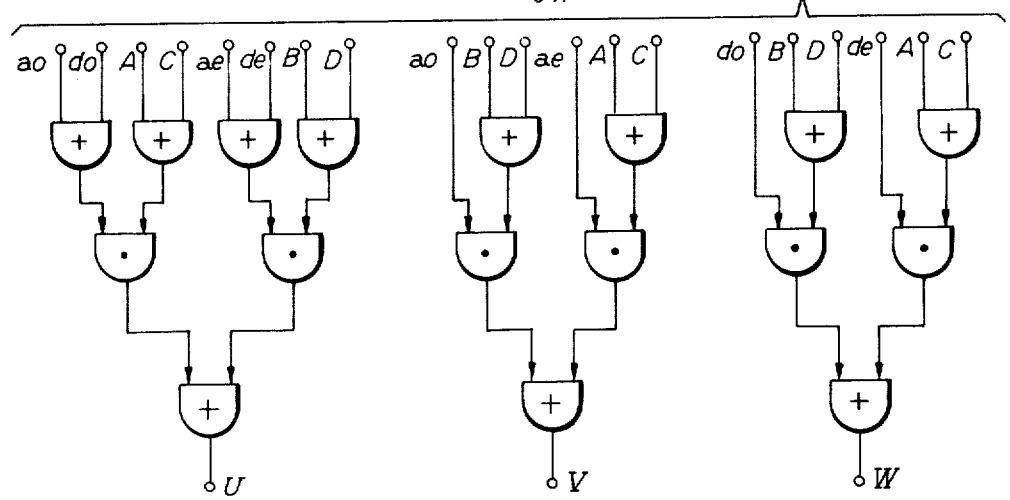
FIG. 17 is a logic diagram illustrating the operation of the circuitry that determimes whether a valid address has been assigned to a scintillation occurring in the boundary region between two adjacent vertical sections of the fiber array.

The purpose of this arrangement can be understood by examining the logic diagrams for producing the pulses at U, V and W as shown in FIG. 17. A pulse is produced at U if either (i) a pulse appears on an odd section line (A or C) and on a column line in an odd section (ao or do), or (ii) a pulse appears on an even section line (B or D) and on a column line in an even section (ae or de). Thus, a pulse at U signifies that the signal column pulse belongs to the same section as does the single section pulse, i.e., that the two pulses give a valid address for the scintillation. Under these conditions, the pulse at U opens GATE 132 in FIG. 16 and all pulses are transmitted directly to the output lines ae3, ao3, de3, do3.

The pulse at V is produced if either (i) the section pulse comes from an even section (B or D) while the single column pulse is an odd "a" (ao) pulse, or (ii) the section pulse comes from an odd section (A or C) while the single column pulse is an even "a" (ae) pulse. Under either of these conditions, the "a" pulse does not belong to the section producing the section pulse and a false address would be generated. A valid address can be obtained, however, by replacing the "a" pulse with its neighboring "d" pulse which lies in the correct section, i.e., ae is replaced by do and ao is replaced by de. This replacement is accomplished by GATE 130 in FIG. 16 which is opened by a pulse at V. The output of GATE 130 is connected so that a pulse on line ae will be interpreted as a pulse on line do. Similarly, a pulse on line ao will be interpreted as a pulse on line de.

If the column pulse is on a d-line which does not correspond to the even or odd section line pulse, a pulse is generated at W (see FIG. 17). The W pulse then opens GATE 134 which in the same manner as GATE 130 replaces the d-line with its neighboring a-line so that the column pulse will have an address consistent with the section pulse.

The output lines from TRANSLATE 68 (see FIG. 7) are, therefore, the section lines A2, B2, C2, D2 (see FIG. 14), and the column lines a3, d3 (see FIG. 16). In addition, there are column lines b and c which are output from GATE 60 (see FIG. 7). Column lines b and c will be referred to as b3 and c3 upon input into the BINARY CONVERSION processors 72 and 74.

The result of the signal processing in TRANSLATE 68 (see FIG. 7) has been (i) to remove all cases in which a pulse appears on more than one of the section lines A, B, C, or D; (ii) to make all column addresses valid by combining the two types of "a" and "d" pulses; and (iii) to allow for the possibility of the appearance of one pulse or two simultaneous pulses on adjacent column lines a, b, c, d (see FIG. 8). By allowing for simultaneous pulses on adjacent lines, it is possible to obtain in the next processing stage a scintillation address that is the average address of the adjacent fiber locations that transmitted the scintillation light.

The preceding description of TRANSLATE 68 also applies to TRANSLATE 70 in FIG. 7. For TRANSLATE 70, the input lines will be 1e, 2, 3, 4e, 1o, 4o, I, II, III, IV rather than ae, b, c, de, ao, do, A, B, C, D; otherwise, the two circuits TRANSLATE 69 and TRANSLATE 70 will be the same. TRANSLATE 70 solves the problem presented by the fact that scintillations occurring near the adjacent boundaries of horizontal sections 34 of the scintillator 16 can produce false addresses in the same manner as that previously described for scintillations occurring near the seams 84 of the vertical sections of the fiber array 18.

D. BINARY CONVERSION Circuits

Figure 18:
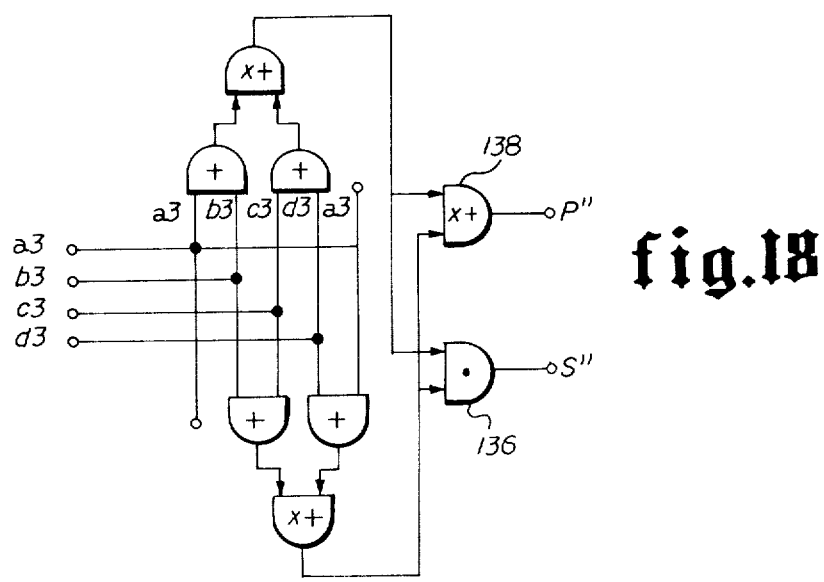
FIG. 18 is a logic diagram illustrating the operation of the circuitry that selects single logic pulses and adjacent pairs of logic pulses.

Since either a single pulse or a pair of pulses may be on lines a, b, c, d, it is convenient to generate flag pulses which will indicate whether one or two pulses are on the lines. The logic diagram in FIG. 18 (which is identical to FIG. 9 for the section lines) shows how these pulses are generated in the BINARY CONVERSION processor 72 (see FIG. 7). A single pulse on any line a3, b3, c3, d3 is passed by the OR and XOR gates so that AND gate 136 produces an output pulse at S'. On the other hand, if there are two pulses on adjacent lines, one of the XOR gates will have pulses on both inputs and will block pulses in that part of the circuit so that AND gate 136 will not open. However, XOR gate 138 will open and a pulse will appear at P'.

Figure 19:
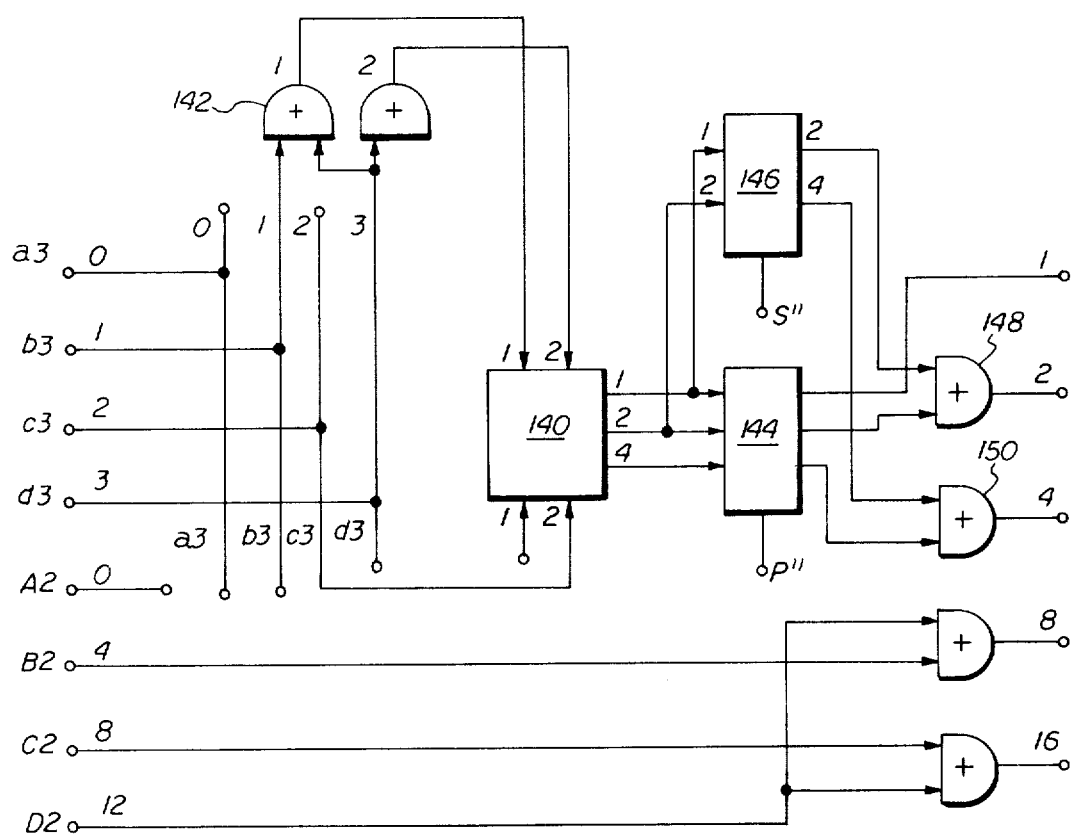
FIG. 19 is a logic diagram illustrating the operation of the circuitry that converts scintillation addresses to binary form.

The diagram in FIG. 19 shows how the pulses on lines a3, b3, c3, d3, A2, B2, C2, D2, are finally converted to a binary column address. The circuit is designed to produce a binary address from pulses on the odd column lines (a3 and c3) and another binary address from the pulses on the even column lines (b3 and d3). This procedure separates the pulses on adjacent lines so that each pulse will give a valid binary address. The odd and even addresses are then added together to give a value that is twice the average address of the two columns locating the scintillation. If only one pulse is present, its binary column address is doubled to give twice the address of the column locating the scintillation.

The preferred embodiment of the means for carrying out these operations is shown in the logic diagram FIG. 19. The four column lines a3, b3, c3, d3 are connected to vertical lines labelled with numbers 0, 1, 2, 3 that now replace the letters. The four section lines A2, B2, C2, D2 are connected to lines labelled with numbers 0, 4, 8, 12. The numbers provide a system of sequential addresses for the fiber matrix columns. For example, column Ac has address 2 (0+2) and column Cd has address 11 (8+3). These addresses are first adjusted to obtain the doubled value discussed above and then converted to binary form for further processing.

The numbers associated with the column input lines a2, b3, c3, d3 are represented in binary form for input into the adder 140. Note that both line b3 and line d3 utilize OR gate 142. This is allowable since there will never be a case wherein nonadjacent columns must be added. After the binary forms of the numbers 0, 1, 2, 3 are added in adder 140, the output lines of the adder 140 carry the result to GATES 144 and 146.

If there is a pair of pulses on lines a3, b3, c3, d3, then there is a pulse on line P" (see FIG. 18) and the binary lines 1, 2, 4 are connected directly through GATE 144. If there is only one pulse on lines a3, b3, c3, d3, then there is a pulse on line S" (see FIG. 18) and GATE 146 is opened. In this case, the output line of GATE 146 associated with binary line 1 is connected to OR gate 148 and the output line of GATE 146 associated with binary line 2 is connected to OR gate 150. In this manner the address for the single pulse is multiplied by two. The binary outputs from GATES 144 and 146 are then combined in the OR gates 148 and 150. The outputs of these OR gates and the output of line 1 from GATE 144 constitute the last three bits of the binary column address of the location of the scintillation producing the pulses. This binary address is twice the address given by the pulses on the input lines a3, b3, c3, d3.

The remaining bits of the doubled address are provided by a single pulse on one of the section lines A2, B2, C2, D2. As discussed above, these four lines have binary addresses 0, 4, 8 and 12 respectively. As shown at the bottom of FIG. 19, these numbers are converted to binary form and are doubled simply by re-labelling the output lines of the binary numbers. These doubled numbers then provide the correct additional bits for combination with the first three bits already generated. The five lines 1, 2, 4, 8, 16 in FIG. 19 provide the binary column address represented on the lines a, b, c, d, A, B, C, D.

An equivalent procedure is carried out in BINARY CONVERSION processor 74 (see FIG. 7) to obtain the binary row address from the lines 1, 2, 3, 4, I, II, III IV.

E. DIGITAL TO ANALOG CONVERSION Circuits

The binary addresses from BINARY CONVERSION processors 72 and 74 are used as the two inputs to the DIGITAL TO ANALOG processor 76 which generates the x- and y-analog signals for deflecting the electron beam of CRT 78 (see FIG. 7). As will be shown, the digital to analog conversion process is more complex than the simple conversion of the input binary addresses to analog signals.

Inspection of the right edge of the fiber matrix shown in FIG. 2 shows that the rows of fibers addressed by the numbered lines are uniformly horizontal and that the ends of the rows lie along a vertical direction. Thus, the conversion of these addresses to an analog signal will give the proper signal to apply to the y-deflection plate of CRT 78 to obtain the y-coordinate of the scintillation. Since these "number" addresses were processed in TRANSLATE circuit 70 and converted to binary addresses in BINARY CONVERSION processor 74, the output lines from BINARY CONVERSION processor 74 can be used as the input lines to a digital to analog converter (DAC) 152 (see FIG. 20). The analog signal output from DAC 152 will then supply the y (vertical) deflection voltage for the CRT of the display oscilloscope 26.

Inspection of the top edge of the fiber matrix shown in FIG. 2 shows that the horizontal "letter" addresses do not give the x-coordinates of the fiber matrix. Because the vertical columns of fibers are inclined approximately thirty degrees (30°) to the right of the vertical, the x-coordinate depends on both the "letter" address (such as aB) and on the "number" address. For example, aB2III has a different x-coordinate than aB4II.

Because the sine of thirty degrees (30°) is one-half, the close packed geometry of the fiber matrix allows one to represent the binary address of the x-coordinate as $$x = L + N/2 \qquad (9)$$

where L is the binary address obtained from the "letter" address and N is the binary address obtained from the "number" address. If one takes the lower left corner of the fiber matrix shown in FIG. 2 as the origin of the coordinate system, it is easier to visualize the reason for adding one-half the value of the "number" address to the "letter" address. The "letter" address gives the value of x-coordinate which would be correct if the columns were vertical. The contribution of one-half the "number" address is added to take account of the fact that the slope of the columns causes the true x-coordinate to be further to the right along the x-axis than is indicated by the "letter" address alone. The value of N/2 is seen to arise from the close packed geometry and the resultant inclination angle of thirty degrees (30°) to the right of the vertical. The corrected x-coordinate and the y-coordinate comprise an orthogonal formulation of the address of the detected radiation.

It is seen that if the fiber matrix possesses a geometry that is other than the close packed geometry described in the preferred embodiment of the invention, then the factor multiplying N, the binary address obtained from the "number" address, will be equal to a value other than $\frac{1}{2}$. The particular value of that factor will depend on the particular geometry chosen for arranging the fibers in the fiber matrix.

Figure 20:
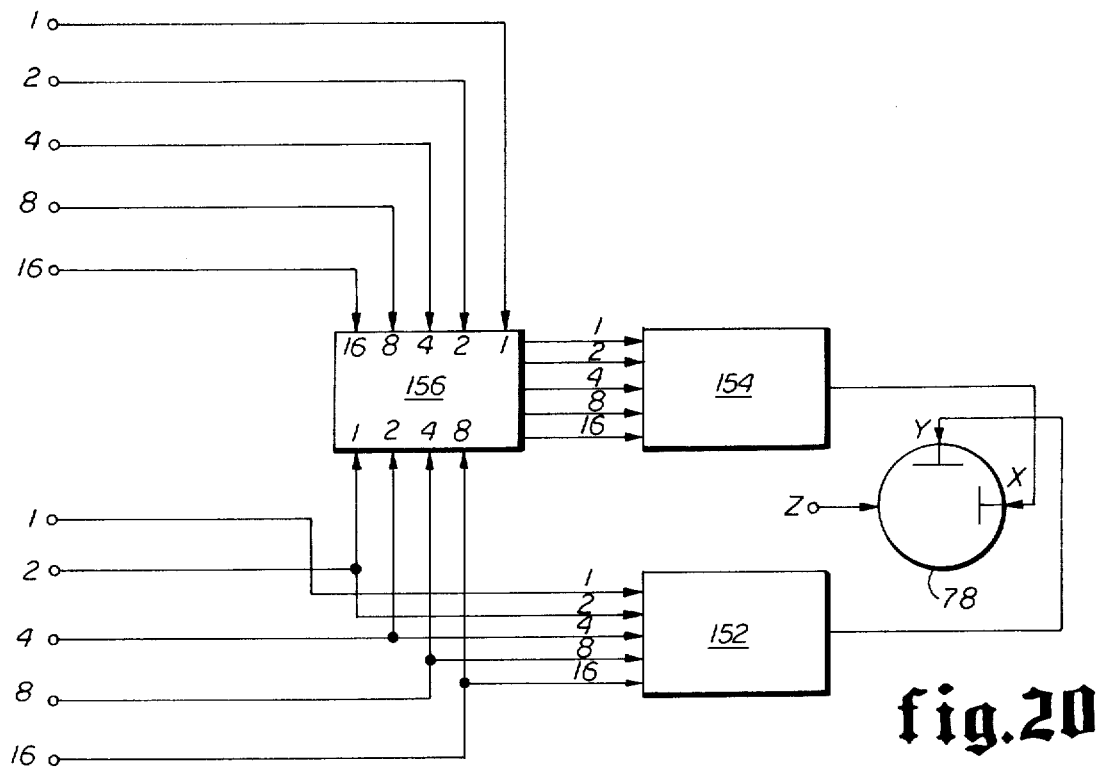
FIG. 20 is a logic diagram illustrating the operation of the circuitry that determines the proper signal to apply to the deflection plates of a cathode ray tube to visually display scintillation locations.

In the preferred embodiment of the invention, the addition of the values L and N/2 is accomplished as shown in FIG. 20. The "letter" address from BINARY CONVERSION processor 72 is one input to adder 156. The "number" address from BINARY CONVERSION processor 74 is divided by two by shifting the lines by one bit upon input to adder 156. The adder output is connected to a digital to analog converter (DAC) 154 which produces the proper signal to apply to the x-deflection plate of CRT 78 to obtain the x-coordinate of the scintillation.

Referring to FIG. 20, note that adder 156 has the same number of bits for the output as it has for the input. This means that if the sum of the two input numbers exceeds thirty-one (31), then the overflow bit which would represent the value 32 is lost and the address begins at zero once more. This permits the addressing of those fiber matrix locations which lie to the left of column aA in FIG. 2.

For example, consider the location cC21V. Since the 16 values of the binary fiber addresses range from 0 to 15, column cC has the value 10. Because adder 156 adds twice the value of the fiber address, L=20. The binary fiber address for row 2IV is 13 and its doubled value is N=26. The x-coordinate calculated from the expression L+N/2 would be 20+26/2=33. Since adder 156 resets the value to zero for x=32, the x-coordinate is really x-1. This represents the distance of one-half fiber diameter and correctly locates the x-coordinate of location cC2IV.

OTHER EMBODIMENTS OF THE CODING SYSTEM

A completely detailed fiber matrix coding system has been described for a 16×16 fiber matrix. The coding system of the present invention is easily extended to an m x n fiber matrix if m and n have values such that $$m = 2^a \times 2^b \quad n = 2^c \times 2^d \tag{10}$$

where a, b, c and d are integers. Under these conditions, the number of columns (and rows) and the number of column sections (and row sections) will have the values 1, 2, 4, 8, 16, 32, etc. Utilization of matrix parameters based on base 2 makes address manipulation convenient and simple.

It is recognized, however, that standard logic circuitry can be used to implement the present coding system equally well for fiber arrays of odd dimensions.

Thus, while the invention has been particularly shown and described with reference to a preferred embodiment thereof, it will be understood by those skilled in the art that the foregoing and other changes in form and detail may be made therein without departing from the spirit and scope of the invention.

What is claimed is:

1. An apparatus for analyzing a radiation image comprising:
   input means for receiving radiation in the pattern of an image to be reproduced and for converting said radiation pattern into a light pattern;
   first coding means for conducting said light pattern from the input means and for coding portions of the light pattern in combinations indicative of the relative positions of said portions of the light pattern wherein said first coding means comprises a plurality of light transmitting elements;
   second coding means for conducting said light pattern from the input means and for coding portions of the light pattern in combinations indicative of the relative positions of said portions of the light pattern wherein said second coding means comprises a plurality of light transmitting conduits;
   output means for receiving said coded portions of the light pattern from the first coding means and from the second coding means and for converting said coded portions of the light pattern into electrical signals; and
   means for determining the relative positions of said portions of said light pattern from the electrical signals provided by the output means to locate the detected incident radiation indicated by the light pattern.

2. An apparatus for analyzing a radiation image comprising:
   input means for receiving radiation in the pattern of an image to be reproduced and for converting said radiation pattern into a light pattern;
   first coding means for conducting said light pattern from the input means and for coding portions of the light pattern in combinations indicative of the relative positions of said portions of the light pattern wherein said first coding means comprises a plurality of light transmitting elements arranged in columns of n elements and in rows of m elements thereby forming an array with a total of n times m elements;
   second coding means for conducting said light pattern from the input means and for coding portions of the light pattern in combinations indicative of the relative positions of said portions of the light pattern wherein said second coding means comprises a plurality of light transmitting conduits;
   output means for receiving said coded portions of the light pattern from the first coding means and from the second coding means and for converting said coded portions of the light pattern into electrical signals; and
   means for determining the relative positions of said portions of said light pattern from the electrical signals provided by the output means to locate the detected incident radiation indicated by the light pattern within an area approximately equal to the cross-sectional area of one of the n times m elements of the array of light transmitting elements of the first coding means.

3. An apparatus for analyzing a radiation image comprising:
   input means for receiving radiation in the pattern of an image to be reproduced and for converting said radiation pattern into a light pattern;
   first coding means for conducting said light pattern from the input means and for coding portions of the light pattern in combinations indicative of the relative positions of said portions of said light pattern wherein said first coding means comprises a plurality of light transmitting elements, said elements arranged in columns of n elements and in rows of m elements thereby forming an array with a total of n times m elements;
   second coding means for conducting said light pattern from the input means and for coding portions of the light pattern in combinations indicative of the relative positions of said portions of said light pattern wherein said second coding means comprises a plurality of light transmitting conduits;
   output means for receiving said coded portions of the light pattern from the first coding means and from the second coding means and for converting said coded portions of the light pattern into electrical signals; and
   means for determining the relative positions of said portions of said light pattern from the electrical signals provided by the output means to locate the detected incident radiation indicated by the light pattern.

4. An apparatus for analyzing a radiation image comprising:
   input means for receiving radiation in the pattern of an image to be reproduced and for converting said radiation pattern into a light pattern;
   first coding means for conducting said light pattern from the input means and for coding portions of the light pattern in combinations indicative of the relative positions of said portions of said light pattern wherein said first coding means comprises a plurality of light transmitting elements, said elements arranged in columns of n elements and rows of m elements thereby forming an array with a total of n times m elements;
   second coding means for conducting said light pattern from the input means and for coding portions of the light pattern in combinations indicative of the relative positions of said portions of said light pattern wherein said second coding means comprises a plurality of light transmitting conduits;
output means for receiving said coded portions of the light pattern from the first coding means and from the second coding means and for converting said coded portions of the light pattern into electrical signals wherein said output means comprises a plurality of light converting output elements with a first selected part of the output elements connected to a number of the total n times m elements of the first coding means, wherein said first selected part of the output elements addresses a particular group of columns of the elements of the first coding means, and with a second selected part of the output elements connected to a number of the total n times m elements of the first coding means, wherein second selected part of the output elements addresses a particular column in a group of columns of the elements of the first coding means, and with a third selected part of the output elements connected to a number of the total n times m elements of the first coding means, wherein said third selected part of the output elements addresses a particular row in a group of rows of the elements of the first coding meeans, and with a fourth selected part of the output elements connected to the light transmitting conduits of the second coding means, wherein said fourth selected part of the output elements addresses a particular group of rows of the elements of the first coding means; and means for determining the relative positions of said portions of said light pattern from the electrical signals provided by the output means to locate the detected incident radiation indicated by the light pattern within an area approximately equal to the cross-sectional area of one of the n times m elements of the first coding means.

5. Apparatus as claimed in claim 4 wherein the means for determining the relative positions of the said portions of said light pattern from the electrical signals provided by the output means to locate the detected incident radiation indicated by the light pattern within an area approximately equal to the cross-sectional area of one of the n times m elements of the first coding means comprises:

means for selecting those electrical signals giving the radiation address of detected incident radiation and for selecting those electrical signals giving two radiation addresses only when those two radiation addresses refer to adjacent sections of the first coding means;

means for resolving ambiguity in ambiguous radiation addresses;

means for obtaining a binary formulation of radiation addresses;

means for obtaining an orthogonal formulation of the binary form of radiation addresses; and visual display means for displaying the light pattern corresponding to the pattern of incident radiation.

6. Apparatus as claimed in claim 5 wherein the means for selecting those electrical signals giving the radiation address of detected incident radiation and for selecting those electrical signals giving two radiation addresses only when those two radiation addresses refer to adjacent sections of the first coding means comprise:

first circuit means having input signal lines in which each input signal line of said first circuit means is connected to and may receive logic pulses produced by electrical signals from any of the output elements connected to a particular group of columns of the light transmitting elements of the first coding means; and in which the input signal lines of said first circuit means connected to the various groups of columns of said light transmitting elements of the first coding means are connected to OR circuits so that each OR circuit has inputs from adjacent groups of columns of the light transmitting elements of the first coding means; and in which the output from pairs of OR circuits serve as input to EXCLUSIVE OR circuits; and in which the output from the EXCLUSIVE OR circuits serve as input to both an AND circuit and an EXCLUSIVE OR circuit connected in parallel; and in which the output from said AND circuit and said EXCLUSIVE OR circuit serve as input to an OR circuit; and in which the output from said OR circuit denotes the presence of logic signals corresponding to the detection of incident radiation in only one group of columns of light transmitting elements or in two adjacent groups of columns of light transmitting elements; and second circuit means having input signal lines in which each input signal lines of said second circuit means is connected to and may receive logic pulses produced by electrical signals from any of the output elements connected to a particular column in a group of columns of light transmitting elements of the first coding means; and in which the input signal lines of said second circuit means connected to the various columns of said light transmitting elements of the first coding means are connected to OR circuits so that each OR circuit has inputs from adjacent columns of said light transmitting elements; and in which the output from pairs of OR circuits serve as input to EXCLUSIVE OR circuits; and in which the output from the EXCLUSIVE OR circuits serve as input to both an AND circuit and an EXCLUSIVE OR circuit connected in parallel; and in which the output from said AND circuit and said EXCLUSIVE OR circuit serve as input to an OR circuit; and in which the output from said OR circuit denotes the presence of logic signals corresponding to the detection of inci dent radiation in only one column of light transmitting elements or in two adjacent columns of light transmitting elements.

7. Apparatus as claimed in claim 5 wherein the means for resolving ambiguity in ambiguous radiation addresses comprises:

means for indicating whether a single logic pulse has been produced by an electrical signal from a single light transmitting element or whether a pair of logic pulses have been produced by electrical signals from two light transmitting elements located in adjacent sections of the first coding means;

means for indicating whether a single logic pulse has been produced by an electrical signal from one of the light transmitting elements in a column of such elements adjacent to a boundary between adjacent sections of the first coding means or whether a pair of logic pulses have been produced by electrical signals from two light transmitting elements, in which one of the elements is located in a column of light transmitting elements adjacent to a boundary between adjacent sections of the first coding means and the other of the elements is located in the column of light transmitting elements immediately on the other side of said boundary; and means for analyzing logic pulses on the signal lines connected to various sections of the first coding means and for analyzing logic pulses on the signal lines connected to the columns of light transmitting elements adjacent to a boundary between adjacent sections of the first coding means, said analysis being made electronically for the four possible combinations of single and paired logic pulses for each of the two aforesaid types of signals to produce a correct unambiguous radiation address in each case.

8. Apparatus as claimed in claim 7 wherein the means for indicating whether a single logic pulse has been produced by an electrical signal from a single light transmitting element or whether a pair of logic pulses has been produced by electrical signals from two light transmitting elements located in adjacent sections of the first coding means comprises:

circuit means having input signal lines in which each input signal line of said circuit means is connected to and may receive logic pulses produced by electrical signals from any of the output elements connected to a particular column in a group of columns of the light transmitting elements of the first coding means; and in which the input signal lines of said circuit means connected to the various columns of said light transmitting elements of the first coding means are connected to OR circuits so that each OR circuit has inputs from adjacent columns of said light transmitting elements; and in which the output from pairs of OR circuits serve as input to EXCLUSIVE OR circuits; and in which the output from the EXCLUSIVE OR circuits serve as input to both an AND circuit and an EXCLUSIVE OR circuit connected in parallel; and in which the output from said AND circuit and said EXCLUSIVE OR circuit serve as input to an OR circuit; and in which the output from said OR circuit denotes the presence of logic signals corresponding to the detection of incident radiation in only one column of light transmitting elements or in two adjacent columns of light transmitting elements.

9. Apparatus as claimed in claim 7 wherein the means for indicating whether a single logic pulse has been produced by an electrical signal from one of the light transmitting elements in a column of such elements adjacent to a boundary between adjacent sections of the first coding means or whether a pair of logic pulses have been produced by electrical signals from two light transmitting elements, in which one of the elements is located in a column of elements adjacent to a boundary between adjacent sections of the first coding means and the other of the elements is located in the column of elements immediately on the other side of said boundary comprises:

circuit means having input signal lines in which each input signal line of said circuit means is connected to and may receive logic pulses produced by electrical signals from the output signal lines corresponding to the columns of light transmitting elements adjacent to a boundary between adjacent sections of the first coding means; and in which the input signal lines are connected to EXCLUSIVE OR circuits and are also connected to AND circuits so that the EXCLUSIVE OR circuits and the AND circuits have inputs from the possible combinations of signals available from the columns of light transmitting elements adjacent to a boundary between adjacent sections of the first coding means which have been denominated as odd or even; and in which the output from the EXCLUSIVE OR circuits serve as input to an OR circuit; and in which the output from that OR circuit denotes the detection of a single logic pulse; and in which the output from the AND circuits serve as input to an OR circuit; and in which the output from that OR circuit denotes the detection of a pair of logic pulses.

10. Apparatus as claimed in claim 7 wherein the means for analyzing logic pulses to produce a correct unambiguous radiation address for each of the four possible combinations of single and paired logic pulses for each of the two types of signals comprises:

first input signal lines connected to sections of the first coding means;

second input signal lines connected to the columns of light transmitting elements adjacent to a boundary between adjacent sections of the first coding means;

control signal lines;

logic gates comprising AND circuits in which one of the inputs to the AND circuits is an input signal line and the other input to the AND circuits is a control signal line; and means for opening or closing the logic gates via the control signal lines in response to the presence of logic pulses on the control signal lines which indicate the existence of a particular combination of single and paired logic pulses or which indicate the existence of a signal on a particular input signal line.

11. Apparatus as claimed in claim 5 wherein the means for obtaining a binary formulation of radiation addresses comprises:

first input signal lines for receiving logic pulses indicating a particular section of the first coding means in a radiation address;

second input signal lines for receiving logic pulses indicating a particular column in a group of columns of light transmitting elements in the first coding means in a radiation address;

output signal lines to which a portion of the first and second input signal lines are connected;

adder means in which logic pulses representing decimal values assigned to odd numbered second input signal lines are received from said odd numbered second input signal lines and combined with logic pulses representing decimal values assigned to even numbered second input signal lines received from said even numbered second input signal lines to yield logic pulses that represent in binary form a value equal to twice the average decimal value of the two decimal values represented by the logic pulses received by said adder means from said odd and even numbered second input signal lines;

logic gates comprising AND circuits responsive to logic ulses on control signal lines that direct the logic pulses from the adder means onto the appropriate output signal lines to double the binary value of the radiation address represented on the second input signal lines when a logic pulse is present only on one second input signal line; and connecting signal lines which connect a portion of the first input signal lines associated with the various sections of the first coding means to the appropriate output signal lines to obtain a doubled value of the radiation address represented on the first input signal lines to form a system of sequential addresses for the columns of light transmitting elements of the first coding means.

12. Apparatus as claimed in claim 5 wherein the means for obtaining an orthogonal formulation of the binary form of radiation addresses comprises:

input signal lines corresponding to the various binary values comprising the "letter" coordinates and the "number" coordinates of the radiation address;

adder means to which said input signal lines are connected and which adds the binary value of a "letter" address to one half the binary value of a "number" address;

a digital to analog converter for converting the binary output signals of said adder means to give an analog representation of the horizontal coordinate of the radiation address; and a digital to analog converter for converting the binary input signals representing a "number" address to an analog representation of the vertical coordinate of the radiation address.

13. An apparatus for analyzing a radiation image comprising input means for receiving radiation in the pattern of an image to be reproduced and for converting said radiation pattern into a light pattern;

first coding means for conducting said light pattern from the input means and for coding portions of the light pattern in combinations indicative of the relative positions of said portions of the light pattern wherein said first coding means comprises a plurality of light transmitting elements, said elements being optically coupled to the input means;

second coding means for conducting said light pattern from the input means and for coding portions of the light pattern in combinations indicative of the relative positions of said portions of the light pattern wherein said second coding means comprises a plurality of light transmitting conduits, said conduits being optically coupled to the input means;

output means for receiving said coded portions of the light pattern from the first coding means and from the second coding means and for converting said coded portions of the light pattern into electrical signals wherein said output means comprises a plurality of light converting output elements with a portion of said output elements connected to the light transmitting elements of the first coding means and with a portion of said output elements connected to the light transmitting conduits of the second coding means;

means for determining the relative positions of said portions of said light pattern from the electrical signals provided by the output means to locate the detected incident radiation indicated by the light pattern; and means for reducing the time required by the light converting output elements of the output means to detect the presence of light in the input means.

14. An apparatus for analyzing a radiation image comprising:

input means for receiving radiation in the pattern of an image to be reproduced and for converting said radiation pattern into a light pattern;

first coding means for conducting said light pattern from the input means and for coding portions of the light pattern in combinations indicative of the relative positions of said portions of the light pattern wherein said first coding means comprises a plurality of light transmitting elements, said elements being optically coupled to the input means and said elements arranged in columns of n elements and in rows of m elements thereby forming an array with a total of n times m elements;

second coding means for conducting said light pattern from the input means and for coding portions of the light pattern in combinations indicative of the relative positions of said portions of the light pattern wherein said second coding means comprises a plurality of light transmitting conduits, said conduits being optically coupled to the input means;

output means for receiving said coded portions of the light pattern from the first coding means and from the second coding means and for converting said coded portions of the light pattern into electrical signals wherein said output means comprises a plurality of light converting output elements with a portion of said output elements connected to the light transmitting elements of the first coding means and with a portion of said output elements connected to the light transmitting conduits of the second coding means;

means for determining the relative positions of said portions of said light pattern from the electrical signals provided by the output means to locate the detected incident radiation indicated by the light pattern within an area approximately equal to the cross-sectional area of one of the n times m elements of the array of light transmitting elements of the coding means; and means for reducing the time required by the light converting output elements of the output means to detect the presence of light in the input means.

15. An apparatus for analyzing a radiation image comprising:

input means for receiving radiation in the pattern of an image to be reproduced and for converting said radiation pattern into a light pattern;

first coding means for conducting said light pattern from the input means and for coding portions of the light pattern in combinations indicative of the relative positions of said portions of said light pattern wherein said first coding means comprises a plurality of light transmitting elements, said elements being optically coupled to the input means and said elements arranged in columns of n elements and in rows of m elements thereby forming an array with a total of n times m elements;

second coding means for conducting said light pattern from the input means and for coding portions of the light pattern in combinations indicative of the relative positions of said portions of said light pattern wherein said second coding means comprises a plurality of light transmitting conduits, said conduits being optically coupled to the input means;

output means for receiving said coded portions of the light pattern from the first coding means and from the second coding means and for converting said coded portions of the light pattern into electrical signals wherein said output means comprises a plurality of light converting output elements with a portion of said output elements connected to the light transmitting elements of the first coding means and with a portion of said output elements connected to the light transmitting conduits of the second coding means;

means for determining the relative positions of said portions of said light pattern from the electrical signals provided by the output means to locate the detected incident radiation indicated by the light pattern; and means for reducing the time required by the light converting output elements of the output means to detect the presence of light in the input means.

16. Apparatus as claimed in claim 15 wherein the means for reducing the time required by the light converting output elements of the output means to detect the presence of light in the input means comprises an optical coupling between the input means and at least one of the light transmitting conduits of the second coding means, said optical coupling having dimensions permitting the collection of light having larger emission angles than the emission angles of light that can be collected by the light transmitting elements of the first coding means thereby permitting a greater amount of light to reach the output elements of the output means connected to the light transmitting conduits of the second coding means than reaches the output elements of the output means connected to the light transmitting elements of the first coding means.

17. Apparatus as claimed in claim 13 or claim 14 wherein said means for reducing the time required by the light converting output elements of the output means to detect the presence of light in the input means comprises an optical coupling between the input means and at least one of the light transmitting elements of said second coding means, said optical coupling having dimensions permitting the collection of light having larger emission angles than the emission angles of light that can be collected by the light transmitting elements of said first coding means thereby permitting a greater amount of light to reach the output elements of the output means connected to the light transmitting elements of said second coding means than reaches the output elements of the output means connected to the light transmitting elements of said first coding means.

18. Apparatus as claimed in claim 1, claim 2, claim 13 or claim 14 wherein said plurality of light transmitting elements of said first coding means and said plurality of light transmitting conduits of said second coding means comprises optical fibers.

19. Apparatus as claimed in claim 1, claim 2, claim 13 or claim 14 wherein said plurality of light transmitting elements of said first coding means and said plurality of light transmitting conduits of said second coding means comprises pieces of solid transparent material.

20. Apparatus as claimed in claim 1, claim 2, claim 13 or claim 14 wherein said plurality of light transmitting elements of said first coding means comprises optical fibers.

21. Apparatus as claimed in claim 1, claim 2, claim 13 or claim 14 wherein said plurality of light transmitting conduits of said second coding means comprises pieces of solid transparent material.

22. Apparatus as claimed in claim 3, claim 4, claim 5, claim 7 or claim 15 wherein said light transmitting elements of said first coding means comprise optical fibers.

23. Apparatus as claimed in claim 3, claim 4, claim 5 claim 7 or claim 15 wherein said light transmitting conduits of said second coding means comprise pieces of solid tranparent material.

24. Apparatus as claimed in claim 3, claim 4, claim 5, claim 7 or claim 15 wherein said light transmitting conduits of said second coding means comprise optical fibers.

25. Apparatus as claimed in claim 4, claim 5, claim 7, claim 13, claim 14 or claim 15 wherein said output elements of said output means comprise photomultipliers.

26. Apparatus as claimed in claim 1, claim 2, claim 3, claim 4, claim 5, claim 7, claim 13, claim 14 or claim 15 wherein said input means comprises a scintillator.

27. An improved method of analyzing a radiation image comprising:
acquiring radiation in an input means in the pattern of an image to be reproduced;
converting said radiation pattern into a light pattern;
coding portions of said light pattern in combinations indicative of the relative positions of said portions of said light pattern utilizing a first coding means comprising a plurality of light transmitting elements and utilizing a second coding means comprising a plurality of light transmitting conduits;
conducting said coded portions of said light pattern to a plurality of light converting output elements;
converting said coded portions of said light pattern into electrical signals; and
determining the relative positions of said portions of said light pattern from said electrical signals to locate the detected incident radiation indicated by the light pattern.

28. An improved method of analyzing a radiation image comprising:
acquiring radiation in an input means in the pattern of an image to be reproduced;
converting said radiation pattern into a light pattern;
coding portions of said light pattern in combinations indicative of the relative positions of said portions of said light pattern utilizing a first coding means comprising a plurality of light transmitting elements formed into an array with columns of n elements and with rows of m elements and utilizing a second coding means comprising a plurality of light transmitting conduits;
conducting said coded portions of said light pattern to a plurality of light converting output elements;
converting said coded portions of said light pattern into electrical signals; and
determining the relative positions of said portions of said light pattern from said electrical signals wherein the location of detected incident radiation indicated by the light pattern is determined to within an area approximately equal to the cross-sectional area of one of the n times m elements of the first coding means.

29. The improved method of analyzing a radiation image as claimed in claim 28 wherein the method of determining the relative positions of said portions of said light pattern from said electrical signals comprises:
selecting those electrical signals giving the address of detected incident radiation;

selecting those electrical signals giving two radiation addresses only when those addresses refer to adjacent sections of the first coding means;

resolving ambiguity in ambiguous radiation addresses;

obtaining a binary formulation of radiation addresses;

obtaining an orthogonal formulation of the binary form of radiation addresses; and displaying the light pattern corresponding to the pattern of incident radiation.

30. The improved method of analyzing a radiation image as claimed in claim 29 wherein the method of resolving ambiguity in ambiguous radiation addresses comprises:

determining whether a single logic pulse has been produced by an electrical signal from a single light transmitting element or whether a pair of logic pulses have been produced by electrical signals from two light transmitting elements located in adjacent sections of the first coding means;

determining whether a single logic pulse has been produced by an electrical signal from one of the light transmitting elements in a column of such elements adjacent to a boundary between adjacent sections of the first coding means or whether a pair of logic pulses have been produced by electrical signals from two light transmitting elements, in which one of the elements is located in a column of elements adjacent to a boundary between adjacent sections of the first coding means and the other of the elements is located in the column of light transmitting elements immediately on the other side of said boundary; and analyzing logic pulses on the signal lines connected to various sections of the first coding means and logic pulses on the signal lines connected to the columns of light transmitting elements adjacent to a boundary between adjacent sections of the first coding means for each of the four possible combinations of single and paired logic pulses for each of the two aforesaid types of signals.

31. The improved method of analyzing a radiation image as claimed in claim 29 wherein the method of obtaining a binary formulation of radiation addresses comprises:

obtaining logic pulses on first input signal lines connected to selected sections of the first input means, wherein said logic pulses represent decimal values of the radiation addresses of said selected sections of the first coding means;

obtaining logic pulses on second input signal lines connected to particular columns in a group of columns of light transmitting elements in the first coding means, wherein said logic pulses represent decimal values of the radiation addresses of said columns of light transmitting elements;

combining logic pulses from odd numbered second input signal lines with logic pulses from even numbered second input signal lines to obtain logic pulses that represent in binary form a value equal to twice the average decimal value of the two decimal values represented by the logic pulses obtained from said odd and even numbered second input signal lines;

directing said combined logic pulses from odd and even numbered second input signal lines onto output signal lines so that the binary value representing a radiation address equal to twice the average of the values of the two radiation addresses represented by the logic pulses from the odd and even numbered second input signal lines is transmitted to said output signal lines;

directing said combined logic pulses from odd and even numbered second input signal lines onto output signal lines so that the binary value representing a radiation address equal to twice the value of a single radiation address that occurs when a logic pulse is present only on one of the second input signal lines connected to said columns of light transmitting elements is transmitted to said output signal lines; and directing said logic pulses on first input signal lines onto output signal lines so that the decimal values assigned to the various sections of the first coding means are doubled in value and are represented in binary form on said output signal lines.

32. The improved method of analyzing a radiation image as claimed in claim 29 wherein the method of obtaining an orthogonal formulation of the binary form of the radiation address comprises:

obtaining logic pulses on input signal lines corresponding to the various binary values comprising the "letter" coordinates of the radiation address;

obtaining logic pulses on input signal lines corresponding to the various binary values comprising the "number" coordinates of the radiation address;

combining logic pulses representing the binary value of the "letter" coordinate of the radiation address with logic pulses representing the binary value of the "number" coordinate of the radiation address to obtain logic pulses that represent the binary value of the sum of the binary value of the "letter" coordinate and one half the binary value of the "number" coordinate;

coverting the logic pulses that represent the binary value of the sum of the binary value of the "letter" coordinate and one half the binary value of the "number" coordinate from a digital representation to an analog representation of the horizontal coordinate of the radiation address; and converting the logic pulses that represent the binary value of the "number" coordinate from a digital representation to an analog representation of the vertical coordinate of the radiation address.

33. An improved method of analyzing a radiation image comprising:

acquiring radiation in an input means in the pattern of an image to be reproduced;

converting said radiation pattern into a light pattern;

coding portions of said light pattern in combinations indicative of the relative positions of said portions of said light pattern utilizing a first coding means comprising a plurality of light transmitting elements and utilizing a second coding means comprising a plurality of light transmitting conduits;

conducting said coded portions of said light pattern to a plurality of light converting output elements;

converting said coded portions of said light pattern into electrical signals;

determining the relative positions of said portions of said light pattern from said electrical signals to locate the detected incident radiation indicated by the light pattern; and reducing the time required by the light converting output elements to detect the presence of light in the input means.

34. An improved method of analyzing a radiation image comprising:
  acquiring radiation in an input means in the pattern of an image to be reproduced;
  converting said radiation pattern into a light pattern;
  coding portions of said light pattern in combinations indicative of the relative positions of said portions of said light pattern utilizing a first coding means comprising a plurality of light transmitting elements formed into an array with columns of n elements and with rows of m elements and utilizing a second coding means comprising a plurality of light transmitting conduits;
  conducting said coded portions of said light pattern to a plurality of light converting output elements;
  converting said coded portions of said light pattern into electrical signals;
  determining the relative positions of said portions of said light pattern from said electrical signals to locate the detected incident radiation indicated by the light pattern; and
  reducing the time required by the light converting output elements to detect the presence of light in the input means.

35. The improved method of analyzing a radiation image as claimed in claim 34 wherein the method of reducing the time required by the light converting output elements to detect the presence of light in the input means comprises:
  optically coupling at least one of the light transmitting conduits of the second coding means to at least one of the surfaces of the input means, said optical coupling having dimensions permitting the collection of light having larger emission angles than the emission angles of light that can be collected by the light transmitting elements of the first coding means; and
  conducting a greater amount of light to the light converting output elements via the light transmitting conduits of the second coding means than can be conducted to the light converting output elements via the light transmitting elements of the first coding means.

36. The improved method of analyzing a radiation image as claimed in claim 33 wherein the method for reducing the time required by the light converting output elements to detect the presence of light in the input means comprises:
  optically coupling at least one of the light transmitting conduits of the second coding means to at least one of the surfaces of the input means, said optical coupling having dimensions permitting the collection of light having larger emission angles than the emission angles of light that can be collected by the light transmitting elements of the first coding means; and
  conducting a greater amount of light to the light converting output elements via the light transmitting conduits of the second coding means than can be conducted to the light converting output elements via the light transmitting elements of the first coding means.

37. The improved method of analyzing a radiation image as claimed in claim 28 with a method for reducing the time required by the light converting output elements to detect the presence of light in the input means comprising:
  optically coupling at least one of the light transmitting conduits of the second coding means to at least one of the surfaces of the input means, said optical coupling having dimensions permitting the collection of light having larger emission angles than the emission angles of light that can be collected by the light transmitting elements of the first coding means; and
  conducting a greater amount of light to the light converting output elements via the light transmitting conduits of the second coding means than can be conducted to the light converting output elements via the light transmitting elements of the first coding means.

38. An improved method of analyzing a radiation image comprising:
  acquiring radiation in a scintillator in the pattern of an image to be reproduced;
  converting said radiation pattern into a light pattern;
  coding portions of said light pattern in combinations indicative of the relative positions of said portions of said light pattern utilizing a first coding means comprising a plurality of optical fibers formed into an array with columns of n optical fibers and with rows of m optical fibers and utilizing a second coding means comprising a plurality of pieces of solid transparent material;
  conducting said coded portions of said light pattern to a plurality of photomultipliers;
  converting said coded portions of said light pattern into electrical signals; and
  determining the relative positions of said portions of said light pattern from said electrical signals wherein the location of detected incident radiation indicated by the light pattern is determined to within an area approximately equal to the cross-sectional area of one of the n times m optical fibers of the first coding means.

39. The improved method of analyzing a radiation image as claimed in claim 38 wherein the method of determining the relative positions of said portions of said light pattern from said electrical signals comprises:
  selecting those electrical signals giving the address of detected incident radiation;
  selecting those electrical signals giving two radiation addresses only when those addresses refer to adjacent sections of the first coding means;
  resolving ambiguity in ambiguous radiation addresses;
  obtaining a binary formulation of radiation addresses;
  obtaining an orthogonal formulation of the binary form of radiation addresses; and
  displaying the light pattern corresponding to the pattern of incident radiation.

40. An improved method of analyzing a radiation image comprising:
  acquiring radiation in a scintillator in the pattern of an image to be reproduced;
  converting said radiation pattern into a light pattern;
  coding portions of said light pattern in combinations indicative of the relative positions of said portions of said light pattern utilizing a first coding means comprising a plurality of optical fibers formed into an array with columns of n optical fibers and with rows of m optical fibers and utilizing a second coding means comprising a plurality of pieces of solid transparent material;

conducting said coded portions of said light pattern to a plurality of photomultipliers;

converting said coded portions of said light pattern into electrical signals;

determining the relative positions of said portions of said light pattern from said electrical signals to locate the detected incident radiation indicated by the light pattern; and reducing the time required by the photomultipliers to detect the presence of light in the scintillator.

41. The improved method of analyzing a radiation image as claimed in claim 40 wherein the method of reducing the time required by the photomultipliers to detect the presence of light in the scintillator comprises:

optically coupling at least one of the pieces of solid transparent material of the second coding means to at least one of the surfaces of the scintillator, said optical coupling having dimensions permitting the collection of light having larger emission angles than the emission angles of light that can be collected by the optical fibers of the first coding means; and conducting a greater amount of light to the photomultipliers via the pieces of solid transparent material of the second coding means than can be conducted to the photomultipliers via the optical fibers of the first coding means.

42. The improved method of analyzing a radiation image as claimed in claim 38 with a method for reducing the time required by the photomultipliers to detect the presence of light in the scintillator comprising:

optically coupling at least one of the pieces of solid transparent material of the second coding means to at least one of the surfaces of the scintillator, said optical coupling having dimensions permitting the collection of light having larger emission angles than the emission angles of light that can be collected by the optical fibers of the first coding means; and conducting a great amount of light to the photomultipliers via the pieces of solid transparent material of the second coding means than can be conducted to the photomultipliers via the optical fibers of the first coding means.

43. An improved method of analyzing a radiation image comprising:

acquiring radiation in a scintillator in the pattern of an image to be reproduced;

converting said radiation pattern into a light pattern;

coding portions of said light pattern in combinations indicative of the relative positions of said portions of said light pattern utilizing a first coding means comprising a plurality of optical fibers formed into an array with columns of n optical fibers and with rows of m optical fibers and utilizing a second coding means comprising a plurality of optical fibers;

conducting said coded portions of said light pattern to a plurality of photomultipliers;

converting said coded portions of said light pattern into electrical signals; and determining the relative positions of said portions of said light pattern from said electrical signals wherein the location of detected incident radiation indicated by the light pattern is determined to within an area approximately equal to the cross-sectional area of one of the n times m optical fibers of the first coding means.

44. The improved method of analyzing a radiation image as claimed in claim 43 wherein the method of determining the relative positions of said portions of said light pattern from said electrical signals comprises:

selecting those electrical signals giving the address of detected incident radiation;

selecting those electrical signals giving two radiation addresses only when those addresses refer to adjacent sections of the first coding means;

resolving ambiguity in ambiguous radiation addresses;

obtaining a binary formulation of radiation addresses;

obtaining an orthogonal formulation of the binary form of radiation addresses; and displaying the light pattern corresponding to the pattern of incident radiation.

45. An improved method of analyzing a radiation image comprising:

acquiring radiation in a scintillator in the pattern of an image to be reproduced;

converting said radiation pattern into a light pattern;

coding portions of said light pattern in combinations indicative of the relative positions of said portions of said light pattern utilizing a first coding means comprising a plurality of optical fibers formed into an array with columns of n optical fibers and with rows of m optical fibers and utilizing a second coding means comprising a plurality of optical fibers;

conducting said coded portions of said light pattern to a plurality of photomultipliers;

converting said coded portions of said light pattern into electrical signals;

determining the relative positions of said portions of said light pattern from said electrical signals to locate the detected incident radiation indicated by the light pattern; and reducing the time required by the photomultipliers to detect the presence of light in the scintillator.

46. The improved method of analyzing a radiation image as claimed in claim 45 wherein the method of reducing the time required by the photomultipliers to detect the presence of light in the scintillator comprises:

optically coupling at least one of the optical fibers of the second coding means to at least one of the surfaces of the scintillator, said optical coupling having dimensions permitting the collection of light having larger emission angles than the emission angles of light that can be collected by the optical fibers of the first coding means; and conducting a greater amount of light to the photomultipliers via the optical fibers of the second coding means than can be conducted to the photomultipliers via the optical fibers of the first coding means.

47. The improved method of analyzing a radiation image as claimed in claim 43 with a method for reducing the time required by the photomultipliers to detect the presence of light in the scintillator comprising:

optically coupling at least one of the optical fibers of the second coding means to at least one of the surfaces of the scintillator, said optical coupling having dimensions permitting the collection of light having larger emission angles than the emission angles of light that can be collected by the optical fibers of the first coding means; and conducting a greater amount of light to the photomultipliers via the optical fibers of the second coding means than can be conducted to the photomultipliers via the optical fibers of the first coding means.

* * * * *